(12) United States Patent
Low et al.

(10) Patent No.: US 8,795,633 B2
(45) Date of Patent: Aug. 5, 2014

(54) MULTIPHOTON IN VIVO FLOW CYTOMETRY METHOD AND DEVICE

(75) Inventors: Philip Stewart Low, West Lafayette, IN (US); Wei He, West Lafayette, IN (US); Walter Anthony Henne, Jr., Lafayette, IN (US); Derek David Doorneweerd, West Lafayette, IN (US); Ji-Xin Cheng, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 960 days.

(21) Appl. No.: 12/067,734

(22) PCT Filed: Sep. 22, 2006

(86) PCT No.: PCT/US2006/037112
§ 371 (c)(1),
(2), (4) Date: Mar. 21, 2008

(87) PCT Pub. No.: WO2007/038346
PCT Pub. Date: Apr. 5, 2007

(65) Prior Publication Data
US 2008/0254499 A1    Oct. 16, 2008

Related U.S. Application Data

(60) Provisional application No. 60/720,316, filed on Sep. 23, 2005, provisional application No. 60/759,771, filed on Jan. 17, 2006.

(51) Int. Cl.
*A61B 5/00*    (2006.01)
(52) U.S. Cl.
USPC ............................................ 424/9.6; 424/9.1
(58) Field of Classification Search
USPC .................................................. 424/9.1, 9.6
See application file for complete search history.

(56) References Cited

U.S. PATENT DOCUMENTS

| | | |
|---|---|---|
| 2,816,110 A | 12/1957 | Sletzinger et al. |
| 4,577,636 A | 3/1986 | Spears |
| 4,641,650 A | 2/1987 | Mok |
| 4,713,249 A | 12/1987 | Schroder |
| 4,718,417 A | 1/1988 | Kittrell et al. |
| 4,785,806 A | 11/1988 | Deckelbaum |
| 4,817,601 A | 4/1989 | Roth et al. |
| 4,850,351 A | 7/1989 | Herman et al. |
| 4,917,084 A | 4/1990 | Sinofsky |
| 4,950,266 A | 8/1990 | Sinofsky |
| 5,094,848 A | 3/1992 | Brixner |
| 5,108,921 A | 4/1992 | Low et al. |
| 5,140,104 A | 8/1992 | Coughlin et al. |
| 5,192,525 A | 3/1993 | Yang et al. |
| 5,217,456 A | 6/1993 | Narciso |
| 5,266,333 A | 11/1993 | Cady et al. |
| 5,275,594 A | 1/1994 | Baker et al. |
| 5,336,506 A | 8/1994 | Josephson et al. |
| 5,373,093 A | 12/1994 | Vallarino et al. |
| 5,399,338 A | 3/1995 | Born et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,562,100 A | 10/1996 | Kittrell et al. |
| 5,576,305 A | 11/1996 | Ratcliffe |
| 5,688,488 A | 11/1997 | Low et al. |
| 5,753,631 A | 5/1998 | Paulson et al. |
| 5,759,546 A | 6/1998 | Weinberg et al. |
| 5,820,847 A | 10/1998 | Low et al. |
| 6,093,382 A | 7/2000 | Wedeking et al. |
| 6,167,297 A | 12/2000 | Benaron |
| 6,204,371 B1 | 3/2001 | Levinson |
| 6,217,847 B1 | 4/2001 | Contag et al. |
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |
| 6,782,289 B1 | 8/2004 | Strauss |
| 6,960,449 B2 | 11/2005 | Wang et al. |

(Continued)

FOREIGN PATENT DOCUMENTS

| | | |
|---|---|---|
| CA | 2520406 | 10/2004 |
| CA | 2666234 | 5/2008 |

(Continued)

OTHER PUBLICATIONS

Wiener et al. "Targeting dendrimer-chelates to tumors and tumor cells expressing the high-affinity folate receptor", Investigative Radiology, 1997, 32(12):748-754.*
Paulos et al. "Ligand Binding and kinetics of folate receptro recycling in vivo: impact on receptor-mediated drug delivery", Molecular Pharmacology, 66(6):1406-1414.*
correction of 892 dated Mar. 16, 2010: Paulos et al. "Ligand binding and kinetics of folate receptor recycling in vivo: impact on receptor-meditaed drug delivery", Molecular Pharmacology, 2004, 66(6):1406-1414.*

(Continued)

*Primary Examiner* — Bin Shen
(74) *Attorney, Agent, or Firm* — Barnes & Thornburg LLP

(57) ABSTRACT

The invention relates to a method for diagnosing a disease state mediated by pathogenic cells, said method comprising the steps of administering to a patient a composition comprising a conjugate or complex of the general formula Ab-X wherein the group $A_b$ comprises a ligand that binds to the pathogenic cells and the group X comprises an imaging agent, and detecting the pathogenic cells that express a receptor for the ligand using mutiphoton in vivo flow cytometry.

39 Claims, 11 Drawing Sheets

(56) References Cited

U.S. PATENT DOCUMENTS

| | | |
|---|---|---|
| 7,033,594 B2 | 4/2006 | Low et al. |
| 7,128,893 B2 | 10/2006 | Leamon et al. |
| 7,223,380 B2 | 5/2007 | Yang et al. |
| 7,381,535 B2 | 6/2008 | Perez et al. |
| 7,601,332 B2 | 10/2009 | Vlahov et al. |
| 8,383,354 B2 | 2/2013 | Low et al. |
| 2001/0031252 A1 | 10/2001 | Low et al. |
| 2002/0127181 A1 | 9/2002 | Edwards et al. |
| 2002/0192157 A1 | 12/2002 | Low et al. |
| 2003/0162234 A1 | 8/2003 | Jallad |
| 2003/0198643 A1 | 10/2003 | Lu |
| 2003/0219375 A1 | 11/2003 | Piwnica-Worms |
| 2004/0033195 A1 | 2/2004 | Leamon et al. |
| 2004/0057900 A1 | 3/2004 | Edwards et al. |
| 2004/0136910 A1 | 7/2004 | Kennedy et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0227985 A9 | 10/2005 | Green et al. |
| 2005/0244336 A1 | 11/2005 | Low |
| 2006/0002891 A1 | 1/2006 | Pouletty |
| 2006/0067946 A1 | 3/2006 | Low et al. |
| 2006/0134002 A1 | 6/2006 | Lin |
| 2006/0182687 A1 | 8/2006 | Yang et al. |
| 2006/0204565 A1 | 9/2006 | Low et al. |
| 2007/0009434 A1 | 1/2007 | Low et al. |
| 2007/0031334 A1 | 2/2007 | Leamon |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low et al. |
| 2009/0012009 A1 | 1/2009 | Low et al. |
| 2010/0055735 A1 | 3/2010 | Low et al. |
| 2010/0322854 A1 | 12/2010 | Low et al. |

FOREIGN PATENT DOCUMENTS

| | | |
|---|---|---|
| EP | 0220030 | 10/1986 |
| EP | 0273085 | 12/1986 |
| EP | 1940473 | 7/2008 |
| JP | 2774378 | 2/1998 |
| JP | 2003-515570 | 5/2003 |
| RU | 21 23338 | 11/1996 |
| RU | 2101703 | 10/1998 |
| WO | 90/12096 | 10/1990 |
| WO | 91/19501 | 12/1991 |
| WO | 91/19502 | 12/1991 |
| WO | 92/13572 | 2/1992 |
| WO | 96/22521 | 7/1996 |
| WO | WO 96/022521 | 7/1996 |
| WO | 96/36367 | 11/1996 |
| WO | 97/37690 | 10/1997 |
| WO | 98/49196 | 11/1998 |
| WO | 99/41285 | 8/1999 |
| WO | 00/73332 | 12/2000 |
| WO | 01/19320 | 3/2001 |
| WO | 01/019320 | 3/2001 |
| WO | 01/039806 | 6/2001 |
| WO | 01/39806 | 6/2001 |
| WO | 01/47552 | 7/2001 |
| WO | WO 01/47552 | 7/2001 |
| WO | 01/74382 | 10/2001 |
| WO | WO 01/74382 | 10/2001 |
| WO | 01/91807 | 12/2001 |
| WO | 02/087424 | 11/2002 |
| WO | 2002/087424 | 11/2002 |
| WO | 2004/044227 | 5/2004 |
| WO | 2004/069159 | 8/2004 |
| WO | 2004/110250 | 12/2004 |
| WO | 2005/049579 | 6/2005 |
| WO | 2005/067644 | 7/2005 |
| WO | 2005/087275 | 9/2005 |
| WO | 2006/012527 | 2/2006 |
| WO | 2006/034046 | 3/2006 |
| WO | WO 2006/034046 | 3/2006 |
| WO | 2006/065943 | 6/2006 |
| WO | WO 2006/065943 | 6/2006 |
| WO | 2006/071754 | 7/2006 |
| WO | 2006/101845 | 9/2006 |
| WO | 2007/001466 | 1/2007 |
| WO | 2007/006041 | 1/2007 |
| WO | 2007/038346 | 4/2007 |
| WO | 2008/057437 | 5/2008 |
| WO | 2008/098112 | 8/2008 |
| WO | 2008/148001 | 12/2008 |
| WO | 2009/002993 | 12/2008 |
| WO | 2009/026177 | 2/2009 |
| WO | WO 09/026177 | 2/2009 |

OTHER PUBLICATIONS

International Search Report and Written Opinion for PCT/US2006/037112 Nov. 22, 2007.

Barnes, H. H., et al., "Purification of Catechol Siderophores by Boronate Affinity Chromatography: Identification of Chrysobactin From *Erwinia carotovora* subsp. *carotovora* ", 1999, *Kluwer Academic Publishers, BioMetals*, vol. 12, pp. 83-87.

Hanessian, Stephen, "Preparative Carbohydrate Chemistry", 1997 *Marcel Dekker, Inc.*, Book Reference, We will provide a copy of the book if requested.

Iijima, Masatomi, et al., "IC202A, A New Siderophore With Immunosuppressive Activity Produced by *Streptoalloteichus* sp. 1454-19", Jan. 1999, *The Journal of Antibiotics*, vol. 52, No. 1, pp. 20-24.

Kennedy, Michael D., et al., "Evaluation of Folate Conjugate Uptake and Transport by the Choroid Plexus of Mice", May 2003, *Pharmaceutical Research*, vol. 20, No. 5, pp. 714-719.

Lingwood, Clifford A., "Oligosaccharide Receptors for Bacteria: A View to a Kill", 1998, *Biopolymers*, pp. 695-700.

Michelson, Alan D., et al., "Evaluation of Platelet Function by Flow Cytometry", 2000, *Academic Press, Methods*, vol. 21, pp. 259-270.

Ratledge, Colin, et al., "The Occurrence of Carboxymycobactin, The Siderophore of Pathogenic Mycobacteria, As a Second Extracellular Siderophore in *Mycobacterium smegmatis* ", 1996 *Microbiology*, vol. 142, pp. 2207-2212.

Scharfman, Andree, et al., "*Pseudomonas Aeruginosa* Binds to Neoglycoconjugates Bearing Mucin Carbohydrate Determinants and Predominantly to sialyl-Lewis x Conjugates", 1999, *Glycobiology*, vol. 9, No. 8, pp. 757-764.

Westerhof, G. Robbin, et al., "Carrier- and Receptor-Mediated Transport of Folate Antagonists Targeting Folate-Dependent Enzymes: Correlates of Molecular-Structure and Biological Activity", 1995, *Molecular Pharmacology*, vol. 48, pp. 459-471.

U.S. Appl. No. 60/956,489, filed Aug. 17, 2007, Low et al.

U.S. Appl. No. 12/513,028, filed Feb. 11, 2007, Low et al.

Albrecht-Gary et al., "Bacterial Iron Transport: Coordination Properties of Pyoverdin PaA, a Peptidic Siderophore of *Pseudomonas aeruginosa* ", 1994. *Inorg. Chem.*, 33 (26), pp. 6391-6402.

Henne, Walter A., et al., "Synthesis and Activity of a Folate Peptide Camptothecin Prodrug", (Aug. 9, 2006), *Bioorganic & Medicinal Chemistry Letters*, vol. 16, pp: 5350-5355.

Tang, Hailun, et al., "Prostate Targeting Ligands Based on N-Acetylated α-Linked Acidic Dipeptidase", (2003), *Biochemical and Biophysical Research Communications*, vol. 307, pp: 8-14.

Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp: 1917-1926.

U.S. Appl. No. 61/235,220, filed Aug. 19, 2009, Low et al.

U.S. Appl. No. 61/157,847, filed Mar. 5, 2009, Low et al.

NCBI, MeSH definition for Indocarbocyanine Green, 2 pages, Aug. 31, 2008, page 2 incomplete.

Achilefu et al., "Novel Receptor—Targeted Fluorescent Contrast Agents for In Vivo Tumor Imaging", Investigative Radiology, vol. 35, No. 8, pp. 479-485, Aug., 2000.

(56) References Cited

OTHER PUBLICATIONS

Antohe et al., "Increased uptake of folate conjugates by activated macrophages in experimental hyperlipemia", Cell Tissue Research, vol. 320, No. 2, pp. 277-285, May 2005.

Aviram et al., "Intralipid infusion abolishes ability of human serum to cholesterol-load cultured macrophages", Arteriosclerosis, vol. 9, pp. 67-75, 1989.

Ballou et al., "Tumor labeling in vivo using cyanine-conjugated monoclonal antibodies", Cancer Immunol Immunother, vol. 41, pp. 257-263, 1995.

Barrera et al., "Synovial macrophage depletion with clodronate-containing liposomes in rheumatoid arthritis", Arthritis and Reheumatism, vol. 43, pp. 1951-1959, 2000.

Beaumont et al., "Selective Fluorodenitration of Chloronitroaromatics", J. Fluorine Chem., vol. 63, pp. 25-30, 1993.

Bettio et al, "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, 2006.

Bock et al., "Sulfonamide Structure-Activity Relationships in a Cell-Free System. 2. Proof for the Formation of a Sulfonamide-Containing Folate Analog", Journal of Medicinal Chemistry, vol. 17, No. 1, pp. 23-28, 1974.

Boechat et al., Fluorodenitrations Using Tetramethylammonium Fluoride, J. Soc. Chem, Commun., pp. 921-92, 1993.

Boente et al., "Screening, imaging, and Early Diagnosis of Ovarian Cancer", Clinical Obstetrics and Gynecology, vol. 37, No. 2, pp. 377-391, Jun. 1994.

Bonasera et al., "The Synthesis of [26, 27-11 C]Dihydroxyvitamin D3, a Tracer for Positron Emission Tomography (PET), Bioorganic & Medicinal Chemistry", Elsevier Science Ltd., vol. 9, pp. 3123-3128.

Budinger et al., "New Approaches to Targeting Arthritis with Radiopharmaceuticals", The Journal of Rheumatology, 22(1) Supp: 62-67, 1995.

Burke et al., "Book Review. The Macrophage", British Journal of Cancer, vol. 89, p. 421, 2003.

U.S. Appl. No. 12/526,096, filed Aug. 6, 2009, Low et al.

Campbell et al., "Folate-binding Protein is a Marker for Ovarian Cancer", Cancer Research, vol. 51, pp. 5329-5338, Oct. 1991.

Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.

Case, "Ultrasound Physics and Instrumentation, Surgical Clinics of North America", vol. 78, No. 2, pp. 197-217, Apr. 1998.

Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.

Ching-Hsuan Tung et al., "Preparation of a Cathepsin D Sensitive Near-Infrared Fluorescence Probe for Imaging", American Chemical Society, vol. 10, No. 5, pp. 692-696, 1999.

Cochlovius, "Therapeutic Antibodies", Modern Drug Discovery, pp. 33-38, 2003.

Cohen et al., "Screening for ovarian cancer: The role of noninvasive imaging techniques", Am J. Obstet Gynecol., vol. 170, No. 4, pp. 1088-1094, 1994.

Cohen et al., "Three-Dimensional Power Doppler Ultrasound Improves the Diagnostic Accuracy for Ovarian Cancer Prediction", Gynecologic Oncology, vol. 82, pp. 40-48, 2001.

Cox et al., "Anhydrous, Tetrabutylammonium Fluoride: A Mild but Highly Efficient Source of Nucleophilic Fluoride Ion", J. Org. Chem., No. 49, pp. 3216-3219, 1984.

Degrado et al., "Synthesis and Evaluation of (18)F-Labeled Choline Analogs as Oncologic PET Tracers", J. Nuclear Medicine, vol. 42, No. 12, pp. 1805-1814, 2001.

DePriest et al., "Transvaginal Sonography as a Screening Method for the Detection of Early Ovarian Cancer", Gynecologic Oncology, vol. 65, No. G0974705, pp. 408-414, 1997.

Feldman et al., "Anti-TNFa Therapy Is Useful in Rheumatoid Arthritis and Crohn's Disease: Analysis of the Mechanism of Action Predicts Utility in Other Diseases", Transplant. Proc. , 30, pp. 4126-4127, 1998.

Forstner et al., "CT and MRI of ovarian cancer", Abdominal Imaging, vol. 20, pp. 2-8, 1995.

Garg et al., "Fluorine-18 Labeling of Monoclonal Antibodies and Fragments with Preservation of Immunoreactivity", Bioconjugate Chem., vol. 2, No. 1, pp. 44-49, 1991.

Giroldo et al., "An Unusually Fast Nucleophilic Aromatic Displacement Reaction: The Gas-Phase Reaction of Fluoride Ions with Nitrobenzene", Angew. Chem. Int. Ed., No. 43, pp. 3588-3590, 2004.

Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, Apr. 1974.

Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 17(10): 35-39, 1999.

Greenman, Y., et al., "Heterogeneous Expression of Two Somatostatin Receptor Subtypes in Pituitary Tumors," Journal of Clinical Endocrinology and Metabolism, vol. 78, No. 2, pp. 398-403, 1994.

Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.

Harris et al., "Human leukemic models of myelomonocytic development: a review of the HL-60 and U937 cell lines", Journal of Leukocyte Biology, vol. 37., No. 4, pp. 407-422, 1985.

Holmgren et al., "Strategies for the Induction of Immune Responses At Mucosal Surfaces Making Use of Cholera Toxin B Subunit As Immunogen, Carrier, and Adjuvant", Am. J. Trop Med Hyd, 50, pp. 42-54, 1994.

Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.

Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.

Johnstrom et al., "18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2002.

Karlan, "The Status of Ultrasound and Color Doppler Imaging for the Early Detection of Ovarian Cancer", Cancer Investigation, vol. 15, No. 3, pp. 265-269, 1997.

Karlan et al., "Ovarian Cancer Screening: The Role of Ultrasound in Early Detection", Cancer Supplement, vol. 76, No. 10, pp. 2011-2015, Nov. 1995.

Karsten et al., "Towards Usage-Based Accounting: Applying Policy-Based Intelligent Agents, ITC 15". Elsevier Science B.V., pp. 633-642, 1997.

Kennedy et al., "Optical imaging of metastatic tumors using a folate-targeted fluorescent probe", J. of Biomedical Optics, vol. 8, No. 4, pp. 636-641, Oct. 2003.

Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.

Kinne et al., "Macrophage in rheumatoid arthritis", Arthritis Research , vol. 2, No. 3, pp. 189-202, 2000.

Konda et al., "Development of a Tumor-Targeting MR Contrast Agent Using the High-Affinity Folate Receptor", Investigative Radiology, vol. 35, No. 1, pp. 50-57, 2000.

Kramer, "Basic Principles of Magnetic Resonance Imaging", Radiological Clinics of North America, vol. 22, No. 4, pp. 765-778, Dec. 1984.

U.S. Appl. No. 12/601,960, filed Nov. 25, 2009, Low.

Kuroiwa et al., "Development of a Fluorescein Operative Microscope for Use During Malignant Glioma Surgery", Elsevier Science Inc., vol. 50, pp. 41-49, 1998.

(56) References Cited

OTHER PUBLICATIONS

Leamon et al., "Folate-mediated targeting: from diagnosis to drug and gene therapy", DDT vol. 6 No. 1 44-51, Jan. 2001.
Leamon et al., "Synthesis and Biological Evaluation of EC140: A Novel Folate—Targeted Vinca Alkaloid Conjugate", Bioconjugate Chem., vol. 17, No. 5, pp. 1226-1232, 2006.
Leamon et al., "Synthesis and Biologicial Evaluation of EC20: A New Folate-Derived, 99mTc-Based Radiopharmaceutical", Bioconjugate Chemistry, vol. 13, No. 6, pp. 1200-1210, 2002.
Leamon et al., "Selective Targeting of Malignant Cells with Cytotoxin-Folate Conjugates", J. Drug Targeting 2: 101-112, 1994.
Lee et al., "Folic Acid Antagonists. Methotrexate Analogs Containing Spurious Amino Acids. Dichlorohomofolic Acid", Journal of Medicinal Chemistry, vol. 17, No. 3, pp. 326-330, 1974.
Lemaire et al., "Fluorine-18-Altanserin: A Radioligand for the Study of Serotonin Receptors with PET: Radiolabeling and In Vivo Biologic Behavior in Rats", The Journal of Nuclear Medicine. vol. 32, No. 12, pp. 2266-2272, Dec. 1991.
Licha et al., "Hydrophilic Cyanine Dyes as Contrast Agents for Near-infrared Tumor Imaging: Synthesis, Photophysical Properties and Spectroscopic In vivo Characterization", Photochemistry and Photobiology, vol. 72, p. 392-398, 2000.
Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.
Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.
Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, p. 391-400, 1995.
Lu et al., "Folate-Targeted Enzyme Prodrug Cancer Therapy Utilizing Penicillin-V Amidase and a Doxorubicin Prodrug", J. Drug Targeting 7:43-53, 1999.
Mahmood et al, "Near Infrared Optical Imaging for Protease Activity for Tumor Detection", Radiology, 213:866-870, 1999.
Maiman et al., "Laproscopic Excision of Ovarian Neoplasm Subsequently Found to Be Malignant", Obstetrics & Gynecology, vol. 77, No. 4, pp. 563-565, Apr. 1991.
Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.
Mantovani et al., "Folate Binding Protein Distribution in Normal Tissues and Biological Fluids From Ovarian Carcinoma Patients as Detected by the Monoclonal Antibodies Mov 18 and Mov 19", Eur J of Cancer, vol. 30A, p. 363-369, 1994.
Mathias et al., "Preparation of 66Ga- and 68GA-labeled Ga(III)-deferoxamine-folate as potential folate-receptor-targeted PET radiopharmaceuticals", Nuclear Medicine and Biology, vol. 30, pp. 725-731, 2003.
Matsuyama et al., "Clinical significance of the folate receptor beta expression in rheumatoid synovial macrophages", Rheumatoid, Japan College of Rheumatology, 41(2): 265, 2001.
Matsuyama et al., "Activation and pathological significance of macrophages in rheumatoid synovitis", Clinical Immunity, Japan, Kagaku Hyoronsha, Tokyo, 30(2): 214-219, 1998.
Mestas et al. "Of Mice and Not Men: Differences between Mouse and Human Immunology", J. Of Immunology, 172, pp. 2731-2738, 2004.
Mukasa et al., "Function analysis of folate receptor-β in a RA synovial membrane macrophage cell line", Rheumatoid, Japan College of Rheumatology, 40(2): 378, 2000.
Mulherin et al., "Synovial tissue macrophage populations and articular damage in rheumatoid arthritis", Arthritis and Rheumatism, vol. 39, No. 1, pp. 115-124, 1996.
Murakami et al., "18F-Labelled Annexin V: A PET Tracer for Apoptosis Imaging", European Journl of Nuclear Medicine and Molecular Imaging, vol. 31, No. 4, pp. 469-474, Apr. 2004.
Nagayoshi et al., "Effectiveness of Anti-Folate Receptor βAntibody Conjugated with Truncated *Pseudomonas* Exotoxin in the Targeting of Rheumoid Arthritis Synovial Macrophages", Arthritis and Rheumatism, vol. 52, p. 2666-2675, 2005.
Nair et al., "Folate Analogues Altered in the C9-N10 Bridge Region: N10-Tosylisohomofolic Acid and N10- Tosylisohomoaminopterin", Journal of Medicinal Chemistry, vol. 21, No. 7, pp. 673-677.
Nair et al., "Folate Analogues Altered in the C9-N10 Bridge Region. 18. Synthesis and Antitumor Evaluation of 11-Oxahomoaminopterin and Related Compounds", Journal of Medicinal Chemistry, vol. 24, pp. 1068-1073, 1981.
Nair et al., "Folate Analogues. 20. Synthesis and Antifolate Activity of 1, 2, 3, 4, 5, 6, - Hexahydrohomofolic Acid", Journal of Medicinal Chemistry, vol. 26, pp. 135-140, 1983.
Nair et al., "Folate Analogues. 21. Synthesis and Antifolate and Antitumor Activities of N10- (Cyanomethyl)-5,8- dideazafolic Acid", Journal of Medicianal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.
Nakashima-Matsushita et al, "Selective expression of folate receptor beta and its possible role in methotrexate transport in synovial macrophages from patients with rheumatoid arthritis", Arthritis Rheum. 42(8): 1609-1616, 1999.
Nehzat et al. "Four ovarian cancers diagnosised during laproscopic management of 1011 women with adnexal masses", Am J Obstet Gynecol., vol. 167, No. 3, pp. 790-796, Sep. 1992.
Oatis et al., "Synthesis of Quinazoline Analogues of Folic Acid Modified at Position 10", Journal of Medicinal Chemistry, vol. 20, No. 11, pp. 1393-1396, 1977.
Olma et al., "4-[18F]fluorophenyl ureas via carbamate-4-nitrophenyl esters and 4-[18F]Fluoroaniline", Journal of Labeled Compd. And Radiopnarm, vol. 49, pp. 1037-1050, 2006.
Paigen et al., "Variation in susceptibility to atherosclerosis among inbred strains of mice", Atherosclerosis, vol. 57, No. 1, pp. 65-73, 1985.
Pasterkamp et al. "Techniques characterizing the coronary atherosclerotic plaque: Influence on clinical decision making?", J. Amer. Coll. Cardiol. 36:13-21, 2000.
Paulos et al. "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.
Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.
Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.
Rampone et al., "Ovarian cancer screening by transvaginal color Doppler ultrasonography", Minerva Ginecologica, vol. 53, Suppl. 1 al N 1, pp. 125-128, 2001.
Reddy et al., "Optimization of Folate-Conjugated Liposomal Vectors for Folate Receptor-Mediated Gene Therapy", J. Pharm. Sciences 88: 1112-1118, 1999.
Reddy et al., "Folate-Mediated Targeting of Therapeutic and Imaging Agents to Cancers", Critical Reviews In Ther. Drug Carrier Systems 15: 587-627, 1998.
Reddy et al., " Folate receptor specific anti-tumor activity of folate-mitomycin conjugates", Cancer Chemother. Pharmacol., 58(2): 229-36, 2006.
Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.
Roberts, et al., "Folic Acid Analogs. Modifications in the Benzene-Ring Region. 3. Neohomofolic and Neobishomofolic Acids. An

(56) References Cited

OTHER PUBLICATIONS

Improved Synthesis of Folic Acid and Its Analogs". Journal of Medicinal Chemistry, 16(6): 697-699, 1973.
Roberts et al., "Folic Acid Analogs. Modifications in the Benzene-Ring Region. 2. Thiazole Analogs", Journal of Medicinal Chemistry, 15 (12): 1310-1312, 1972.
Roberts et al., "Folic Acid Analogs. Modifications in the Benzene-Ring Region. 1. 2'- and 3'- Azafolic Acids", Journal of Medicinal Chemistry, 14(2): 125-130, 1971.
Roberts et al., "Folic Acid Analogs. Modifications in the Benzene-Ring Region. 4. 3'- Ethyl - and 3'- Isopropylfolic Acids", Journal of Medicinal Chemistry, vol. 17, No. 2, pp. 219-222, 1974.
Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.
Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.
Sato et al., "Usefulness of Mass Screening for Ovarian Carcinoma Using Transvaginal Ultasonography", American Cancer Society, vol. 89, No. 3, pp. 582-588, Aug. 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Jan/Feb 2000.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Sima et al., "Experimental obstructive coronary atherosclerosis in the hyperlipidemic hamster", J Submicrosc Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16.
Sudimak et al., "Targeted drug delivery via the folate receptor", Advanced Drug Delivery Reviews, vol. 41, pp. 147-162, 2000.
Sun et al., "Anhydrous Tetrabutylammonium Fluoride", J. Am. Chem. Soc., vol. 127, No. 7, pp. 2050-2051, 2005.
Sun et al., "Room-Temperature Nucleophilic Aromatic Fluorination: Experimental and Theoretical Studies", Angew. Chem. Int. Ed., No. 45, pp. 2720-2725, 2006.
Sundstrum et al., "Establishment and characterization of a human histiocytic lymphoma cell line (U-937)", International Journal of Cancer, vol. 17, No. 5, pp. 565-577, 1976.
Sutcliffe-Goulden, "Solid Phase Synthesis of [18F]Labelled Peptides for Positron Emission Tomography", Bio. & Medicin. Chem. Letters, No. 10, pp. 1501-1503, 2000.
Tan et al., "A Complete Remote-Control System for Reliable Preparation of [18F]altanserin", Applied Radiation and Isotopes, vol. 50, pp. 923-927, 1999.
Temple, Jr. et al., "Synthesis of Pseudo Cofactor Analogues as Potential Inhibitors of the Folate Enzymes", Journal of Medicinal Chemistry, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74., pp. 193-198, 1997.
Turk et al., "Folate-targeted imaging of activated macrophage in rats with adjuvant-induced arthritis", Arthritis and Rheumatism, vol. 46, No. 7, pp. 1947-1955, 2002.
Urban, "Screening for ovarian cancer: We now need a definitive randomized trial", BMJ, vol. 319, pp. 1317-1318, Nov. 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Wang et al. "Synthesis, Purification, and Tumor Cell Uptake of 67-Ga-Deferoxamine-Folate, a Potential Radiopharmaceutical for Tumor Imaging", American Chemical Society, Bioconjugate Chem., 1996, 7(1): 56-62, 1996.
Weinstock et al., "Folic Acid Analogs. II. p-{[2,6-Diamino-8-purinyl)methyl]amino} - benzoyl-L-glutamic Acid and Related Compounds", Journal of Medicinal Chemistry, 1970, 13(5): 995-997, 1970.
Weissleder et al., "In vivo imaging of tumors with protease-activated near-infrared fluorescent probes", Nature Biotechnology, vol. 17, pp. 375-378, Apr. 1999.
Weitman et al., "The folate receptor in central nervous system malignancuies of childhood", Journal of Neuro-Oncology, vol. 21, pp. 107-112, 1994.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, 1999.
Yavorsky et al. "Antiparticles", Handbook on Physics, pp. 339-340, 1984.
Zeisel et al., "Choline, an Essential Nutrient for Humans", The Faseb Journal, vol. 5, No. 7, pp. 2093-2098, 1991.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.
Patrick et al., "Folate receptors as potential therapeutic targets in choroid plexus tumors of SV40 transgenic mice", Journal of Neuro-Oncology, 32: 111-123, 1997.
Weitman et al., "Distribution of the folate receptor GP38 in normal and malignant cell lines and tissues" Cancer Research, 52: 3396-3401, 1992.
Mathias et al., "Indium-111-DTPA-folate as a potential folate-receptor-targeted radiopharmaceutical", Journal of Nuclear Medicine, 39: 1579-1585, 1998.
Acosta et al., "Chromoendoscopy—where is it useful?", Journal of Clinical Gastroenterology, 27:13-20,1998.
Fleischer, "Chromoendoscopy and magnification endoscopy in the colon", Gastrointestinal Endoscopy, 49: S45-49, 1999.
Stepp et al., "Fluorescence endoscopy of gastrointestinal diseases: basic principles, techniques, and clinical experience", Endoscopy, 30: 379-386, 1998.
Ballou et al., "Tumor detection and visualization using cyanine fluorochrome-labeled antibodies", Biotechnology Progress, 13: 649-658, 1997.
Licha et al., "Synthesis, characterization, and biological properties of cyanine-labeled somatostatin analogues as receptor-targeted fluorescent probes", Bioconjugate Chemistry, 12: 44-50, 2001.
Becker et al., "Receptor-targeted optical imaging of tumors with near-infrared fluorescent ligands", Nature Biotechnology, 19: 327-331, 2001.
Terpetschnig et al., "Synthesis of squaraine-N-hydroxysuccinimide esters and their biological application as long-wavelength fluorescent labels", Analytical Biochemistry, 217: 197-204, 1994.
Mujumdar et al., "Cyanine dye labeling reagents containing isothiocyanate groups", Cytometry, 10:11-19, 1989.
Wang et al., "Design and synthesis of [111 In]DTPA-folate for use as a tumor-targeted radiopharmaceutical", Bioconjugate Chemistry, 8: 673-679, 1997.

(56) References Cited

OTHER PUBLICATIONS

Dimartino et al., "Antiarthritic and immunoregulatory activity of spirogermanium", Journal of Pharmacology an Experimental Therapeutics, 236: 103-110, 1986.
Ross et al., "Differential regulation of folate receptor isoforms in normal and malignant tissues in vivo and in established cell lines. Physiologic and clinical implications", Cancer, 73: 2432-2443, 1994.
Ross et al., "Folate receptor type beta is a neutrophilic lineage marker and is differentially expressed in myeloid leukemia", Cancer, 85: 348-357, 1999.
Curtin et al., "Stage IV ovarian cancer: impact of surgical debulking", Gynecologic Oncology, 64: 9-12, 1997.
Munkarah et al., "Prognostic significance of residual disease in patients with stage IV epithelial ovarian cancer", Gynecologic Oncology, 64:13-17, 1997.
Murolo et al., "Ultrasound examination in ovarian cancer patients. A comparison with second look laparotomy", Journal of Ultrasound in Medicine, 8: 441-443, 1989.
Piver et al., "Second-look laparoscopy prior to proposed second-look parotomy", Obstetrics and Gynecology, 55: 571, 1980.
Bell et al., "Intraoperative radioimmunodetection of ovarian cancer using monoclonal antibody B72.3 and a portable gamma-detecting probe", Obstetrics and Gynecology, 76: 607-677, 1990.
Reuter et al., "Detection of colorectal carcinomas by intraoperative RIS in addition to preoperative RIS: surgical and immunohistochemical findings", European Journal of Nuclear Medicine, 19: 102-109, 1992.
Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.
Folli et al., "Immunophotodiagnosis of colon carcinomas in patients injected with fluoresceinated chimeric antibodies against carcinoembryonic antigen", Proc Nat Academy of Sciences U.S.A., 89: 7973-7977, 1992.
Folli et al., "Antibody-indocyanin conjugates for immunophotodetection of human squamous cell carcinoma in nude mice", Cancer Research, 54: 2643-2649, 1994.
Bannwarth et al., "Methotrexate in rheumatoid arthritis. An update", Drugs, 47: 25-50, 1994.
Bettegowda, et al., "Imaging bacterial infections with radiolabeled 1-(2[-deoxy-2[-fluoro- [-D-arabinofuranosyl)-5-iodouracil," Proc. Natl. Acad. Sci U.S.A., 102: 1145-1150, 2005.
Bunce et al., "Murine Model of Cutaneous Infection with Gram-Positive Cocci," Infect. Immun., 60: 2636-2640, 1992.
Claassen E. et al., "Preparation and characteristics of dichloromethylene diphosphonate-containing liposomes," J. Microencapsul., 3: 109-14, 1986.
Marceau et al., "Efficient synthesis of C-terminal modified peptide ketones for chemical ligations," Bioorganics and Medical Chemistry Letters, 15(24): 5442-5445, 2005.
Novabiochem® Letters, "Resins for the synthesis of biotinylated and fluorescently-labeled peptides," Jan. 2004, pp. 1-4, 2004.
Novabiochem® Letters, "Products for peptide ligation," Feb. 2004, pp. 1-4, 2004.
Novabiochem® Letters, "Amino acids for Fmoc SPPS," Mar. 2004, pp. 1-4, 2004.
Novabiochem® Letters, "PEG reagents," Apr. 2004, pp. 1-4, 2004.
Marecos et al., "Antibody-Mediated versus Nontargeted Delivery in a Human Small Cell Lung Carcinoma Model", Bioconjugate Chemistry, 9:184-191 (1998).
"Osteomyelitis", XP-002569963, URL:http://emedicine.medscape.com/article/785020-overview>, retrieved Feb. 22, 2010.
Kennedy MD, "Folate-targeted imaging agents," Thesis submitted to the faculty of Purdue University in partial fulfillment of the requirements for the degree of Doctor of Philosophy, published Nov. 2004.
Holladay et al., "Riboflavin-mediated delivery of a macromolecule into cultured human cells," Biochim Biophys Acta 1426(1): 195-204 (1999).
Low PS et al. "Folate-mediated delivery of therapeutic and imaging agents to cancer tissue," Gene, Drug Therapy, and Molecular Biology (Abstract), 2000.
Low, P.S. et al., "Folate-Mediated Delivery of Therapeutic and Imaging Agents to Cancer Tissues in Vivo," *International Symposium on Tumor Targeted Delivery Systems*, Bethesda, MD. British J. of Pharmacology, vol. 134 (Abstract), 2001.
Kern MJ et al., "Evaluation of the culprit plaque and the physiological significance of coronary atherosclerotic narrowings," Circulation. 2001;103:3142-3149.
Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.
Bettio et al. "Synthesis and Preclinical Evaluation of a Folic Acid Derivative labeled with 18F for PET Imaging of Folate Receptor-Positive Tumors", The Journal of Nuclear Medicine, vol. 47, No. 7, pp. 1153-1160, 2006.
Bock et al., "Sulfonamide Structure-Activity Relationships in a Cell-Free System 2. Proof for the Formation of a Sulfonamide-Containing Folate Analog", Journal of Medicinal Chemistry, vol. 17, No. 1, pp. 23-28, 1974.
Boechat et al., "Fluorodenitrations Using Tetramethylammonium Fluoride", J. Soc. Chem. Commun. pp. 921-92, 1993.
Boenfe et al., "Screening, imaging, and Early Diagnosis of Ovarian Cancer", Clinical Obstetrics and Gynecology, vol. 37, No. 2, pp. 377-391, Jun. 1994.
Bonasera et al., "The Synthesis of [26, 27-11C]Dihydroxyvitamin D3, a Tracer for Positron Emission Tomography (PET), Bioorganice & Medicinal Chemistry", Elsevier Science Ltd., vol. 9, pp. 3123-3128, 2001.
Budinger et al., "New Approaches to Targeting Arthritis with Radiopharmaceuticals", The Journal of Rheumatology, 22(1) Supp 62-67, 1995.
Burke et al., "Book Review, The Macrophage", British Journal of Cancer, vol. 89, p. 421, 2003.
Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.
Nair et al., "Folate Analogues Altered in the C9-N10 Bridge Region: N10-Tosylisohomofolic Acid and N10-tosyllsohomoaminopterin", Journal of Medicinal Chemistry, vol. 21, No. 7, pp. 673-677, 1978.
Nair et al, "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region, 14. 11-Oxahomofolic Acid, a Potential Antitumor Agent", Journal of Medicinal Chemistry, vol. 23, pp. 59-65, 1980.
Nair et al., "Folate Analogue Altered in the C9-N10 Bridge Region, 18. Synthesis and Antitumor Evaluation of 11-Oxahomoaminopterin and Related Compounds", Journal of Medicinal Chemistry, vol. 24, pp. 1068-1073, 1981.
Nair et al., "Folate Analogues. 20. Synthesis and Antifolate Activity of 1,2,3,4,5,6, - hexahydrohomofolic Acid", Journal of Medicinal Chemistry, vol. 26, pp. 135-140, 1983.
Nair et al., "Folate Analogues. 21. Synthesis and Antifolate and Antitumor Activities of N10- (Cyanomethyl)-5.8-dideazafolic Acid", Journal of Medicinal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.
Sijtsema et al., "Confocal Direct Imaging Raman Microscope: Design and Application in Biology", Applied Spectroscopy, vol. 52, issue 3, pp. 348-355, 1998.
Sima et al., "Experimental obstructive coronary atherosclerosis in the hyperlipidemic hamster", J Submicrose Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16, 1990.

(56) References Cited

OTHER PUBLICATIONS

Smart et al., "Protein kinase C activators inhibit receptor-mediated potocytosis by preventing internalization of caveolae", Journal of Cell Biology, vol. 124, No. 3, pp. 307-313, 1994.
Solomin et al., "Computerized Tomography in Ovarian Cancer", Gynecologic Oncology, vol. 15 pp. 48-55, 1983.
Sudimak et al. "Targeted drug delivery via the folate receptor". Advanced Drug Delivery Reviews, vol. 41, pp. 147-162, 2000.
Sun et al., "Anhydrous Tetrahuiylammonlum Fluoride", J Am. Chem Soc., vol. 127, No. 7, pp. 2050-2051. 2005.
Sun et al., "Room-Temperature Nucleophilic Aromatic Fluorination: Experimental and Theoretical Studies", Angew. Chem. Int. Ed., No. 45, pp, 2720-2725, 2006.
International PCT Search Report and Written Opinion for PCT Application No. PCT/US2004/016667, completed Sep. 22, 2004.
Kilbourn et al, Fluorine-18 labeling of proteins, 1987, J Nucl Med, 28: 462-470.
Coussens et al, Inflammation and cancer, 2002, Nature, 420: 860-867.
PCT International Search Report and Written Opinion for PCT Application No. PCT/US2010/026406, mailed Apr. 15, 2010.
Nisshoshi, 1994, The Japanese Journal of Gastoenterology, 91(2): 131-135.
Extended European Search Report for EP 02734139, completed Jun. 11, 2004.
International PCT Search Report and Written Opinion for PCT Application No. PCT/US2008/053293, completed Mar. 10, 2009.
International PCT Search Report and Written Opinion for PCT Application No. PCT/US2005/046708, completed Sep. 20, 2006.
Extended European Search Report for EP 05855293, completed Jun. 12, 2009.
Extended European Search Report for EP 04753487, completed Jun. 16, 2006.
Extended European Search Report for EP 07867348, completed Jul. 29, 2010.
Nair et al., "Folate Analogues Altered in the C9-N10 Bridge Region. 10-Oxafolic Acid and 10-Oxaaminopterin", Journal of Medicinal Chemistry, vol. 19, No. 6 pp. 825-829, 1976.
Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.
Nair et al., "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.
Nair et al., "Folate Analogues Altered in the C9-N10 Bridge Region. 18. Synthesis and Antitumor Evaluation of 11-Oxahomoaminopterin and Related Compounds", Journal of Medicinal Chemistry, vol. 24, pp. 1068-1073, 1981.
Nair et al., "Folate Analogues. 20. Synthesis and Antifolate Activity of 1,2,3,4,5,6,—Hexahydrohomofolic Acid", Journal of Medicinal Chemistry, vol. 26, pp. 135-140, 1983.
Nair et al., "Folate Analogues. 20. Synthesis and Antifolate and Antitumor Activities of N10-(Cyanomethyl)-5,8-dideazafolic Acid", Journal of Medicinal Chemistry, vol. 26, pp. 605-607, 1983.
Nair et al., "Folate Analogues, 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.
Schalk, Isabelle J., et al., "Iron-Free Pyoverdin Binds To Its Outer Membrane Receptor FpvA In Pseudomonas Aeruginosa: A New Mechanism for Membrane Iron Transport", 2001, *Molecular Microbiology*, vol. 39, No. 2, pp. 351-360.
Albrecht-Gary et al., "Bacterial Iron Transport: Coordination Properties of Pyoverdin PaA, a Peptidic Siderophore of *Pseudomonas aeruginosa*", 1994. *Inorg. Chem.*,33 (26), pp. 6391-6402.

Henne, Walter A., et al., "Synthesis and Activity of a Folate Peptide Camptothecin Prodrug", (Aug. 9, 2006), *Bioorganic & Medicinal Chemistry Letters*, vol. 16, pp. 5350-5355.
Tang, Hailun, et al., "Prostate Targeting Ligands Based on N-Acetylated α-Linked Acidic Dipeptidase", (2003), *Biochemical and Biophysical Research Communications*, vol. 307, pp. 8-14.
Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.
International Search Report and Written Opinion for PCT/US2007/023176 completed Aug. 4, 2008.
Wiener et al., "Targeting Dendrimer—Chelates to Tumors and Tumor Cells Expressing the High-Affinity Folate Receptor," *Investigative Radiology*, 1997; 32(12):748-754.
Paulos et al., "Ligand Binding and Kinetics of Folate Receptor Recycling in Vivo: Impact on Receptor-Mediated Drug Delivery," Molecular Pharmacology, 2004; 66:1406-1414.
He et al., "In vivo quantitation of rare circulating tumor cells by multiphoton intravital flow cytometry," Proc Nat Acad Sci USA, 2007; 104: 11760-11765.
Phelps et al., Journal of Nuclear Medicine, 1975, 16(3): 210-224.
Snook et al., Br. J. Cancer, 1990, 62 (Suppl. X): 89-91.
Patton, Radiographics, 1998, 18: 995-1007.
Chen et al., "In vivo imaging of proteolytic activity in atherosclerosis," Circulation, 2002, 105: 2766-2771.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Virto & In Vivo Studies with α-and γ-Isomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.
Massoud et al., "Molecular imaging in living subjects: seeing fundamental biological processes in a new light", 2003, Genes Dev. 17: 545-580.
Caliceti et al., "Pharmacokinetic and biodistribution properties of poly9ethylene glycol)—protein conjugates", 2003, Adv. Drug Del. Rev. 55: 1261-1277.
Tamaki, et al., "PET in Oncology" Jpn J Cancer Clin, 2003, 49(6): 531-535.
Remington: The Science & Practice of Pharmacy, 21th Edition (Lippincott Williams & Wilkins, 2005).
Bendele et al., "Animal Models of Arthritis: Relevance to Human Disease", Toxicology Pathology, vol. 27, No. 1, pp. 134-142, 1999.
Tanaka, et al., "Digestive tract lesions and immunity," The Japanese Journal of Gastroenterology, 1994, vol. 91(2): 131-135.
Folate-FITC (http://www.medkoo.com/Anticancer-trials/EC-17.htm (downloaded on Aug. 8, 2013)).
Atherosclerosis (http)://web.archive.org/web/20081207060 136/ http://en.wikipedia.org/wiki/Atherosclerosis (archived on Dec. 7, 2008)).
Kanagaki et al., "Pituitary Gland and Parasellar Region," in *Magnetic Resonance Tomography*, Reiser et al. (eds.), 2008, p. 422.
Barnes, H. H., et al., "Purification of Catechol Siderophores by Boronate Affinity Chromatography: Identification of Chrysobactin From *Erwinia carotovora subsp. carotovora*", 1999, *BioMetals*, vol. 12, pp. 83-87.
Collins, Peter, et al., "Monosaccharides, Their Chemistry And Their Roles In Natural Products", 1995 *Wiley Publishers*, Book Reference, We will provide a copy of the book if requested.
Georgakoudi, Irene, et al., "In Vivo Flow Cytometry: A New Method for Enumerating Circulating Cancer Cells", Aug. 1, 2004, *Cancer Research*, No. 64, pp. 5044-5047.
Haness Ian, Stephen, "Preparative Carbohydrate Chemistry", 1997 *Marcel Dekker, Inc.*, Book Reference, We will provide a copy of the book if requested.
Idanpaan-Heikkila, Ilona, et al., "Oligosaccharides Interfere With The Establishment And Progression Of Experimental Pneumococcal Pneumonia", 1997, *The Journal of Infectious Diseases*, No. 176, pp. 704-712.

(56) References Cited

OTHER PUBLICATIONS

Iijima, Masatomi, et al., "IC202A, A New Siderophore With Immunosuppressive Activity Produced By Streptoalloteichus sp. 1454-19. I. Taxonomy, fermentation, isolation and biological activity.", Jan. 1999, *The* .

Lingwood, Clifford A., "Oligosaccharide Receptors For Bacteria: A View To A Kill", 1998, *Curr Opin Chem Biol.*, pp. 695-700.

Michelson, Alan D., et al., "Evaluation Of Platelet Function by Flow Cytometry", 2000, *Methods*, vol. 21, pp. 259-270.

Novak, J., et al., "In Vivo Flow Cytometer For Real-Time Detection And Quantification of Circulating Cells", Jan. 1, 2004 *Optics Letters*, vol. 29, No. 1, pp. 77-79.

Ratledge, Colin, et al., "The Occurrence of Carboxymycobactin, The Siderophore Of Pathogenic Mycobacteria, As A Second Extracellular Siderophore In *Mycobacterium smegmatis*", 1996 Microbiology, vol. 142, pp. 2207-2212.

Scharfman, Andree, et al., Pseudomonas Aeruginosa Binds To Neoglycoconjugates Bearing Mucin Carbohydrate Determinants Glycobiology, 1999,9(8):757-764.

Sudimack et al, Advanced Drug Delivery Reviews, 2000, 41: 147-162.

Ilgan et al., "Imaging tumor folate receptors using 111IN-DTPA-methotrexate." *Cancer Biother. Radiopharm.*,1998, 13(3) pp. 177-184.

Agoston E.S. et al "Vitamin D Analogs as Anti-Carcinogenic Agents" *Anti-Cancer Agents in Medicinal Chemistry* 2006, 6(1), pp. 53-71.

Lonsdale, D., "A Review of the Biochemistry, Metabolism and Clinical Benefits of Thiamin(e) and Its Derivatives." *Evidence-Based Complementary & Alternative Medicine: eCAM*. Advance Access Publication, vol. 3, Feb. 2006, pp. 49-59.

Nosaka, K. et al., "Separate Determination of Anticoccidial Thiamine Analogs by High-Performance Liquid Chromatography." *ActaA Vitaminol. Et Enzymol.,* 1984, vol. 6 92), pp. 137-142.

Kandiko, C.T. et al., "Inhibition of Rat Brain Pyruvate Dehydrogenase by Thiamine Analogs." *Biochem. Pharmacology*, vol. 37, No. 22, (1988) pp. 4375-4380.

Spry, C. et al., "A Class of Pantothenic Acid Analogs Inhibits Plasmodium Falciparum Pantothenate Kinase and Represses the Proliferation of Malaria Parasites." *Antimicrobial Agents and Chemotherapy*, Nov. 2005, pp. 4649.

Sargent, D.R. et al., "Antimetabolites of Pantothenic Acid, Ureido- and Carbamoyl-Derivatives." *Texas Reports on Biology and Medicine*, 1975, vol. 33, No. 3, pp. 433-443.

Hanck, A.B. et al., "Dexpanthenol (Ro 01-4709) in the treatment of constipation." Abstract, Acta Vitaminol Enzymol, 1982, vol. 4 (1-2), pp. 87-97.

Kagechika, H. et al., "Synthetic Retinoids: Recent Developments Concerning Structure and Clinical Utility." *J. Med. Chem.*, Sep. 22, 2005, vol. 48, No. 19, pp. 5875-5883.

Shealy, Y.F. "Synthesis and Evaluation of Some New Retinoids for Cancer Chemoprevention." *Preventive Medicine*, 1989, vol. 18, pp. 624-645.

Renz, P. et al., "Synthesis of 4-Aza-5,6-diethylbenzimidazole and Biosynthetic Preparation of 4- and 7-Aza-5,6-dimethylbenzimidazolylcobamide," *Z Naturforsch*, 1997, vol. 52c, pp. 5287-5291.

Ayers, W.A., "Effect of Vitamin B12 and Analogs on the Respiration of a Marine Bacterium." *Archives of Biochemistry and Biophysics*, 1962, vol. 96, pp. 210-215.

Toraya, T. et al., "Immobilized Derivatives of Vitamin B12 Coenzyme and Its Analogs." *Methods in Enzymology*, 1980, vol. 67, pp. 57-66.

Ueda, M. et al., "Effect of Vitamin B12 Derivatives on Urinary Excretion of Methylmalonic Acid in Liver Diseases." *Acta Med. Okayama*, 1970, vol. 24, pp. 365-372.

Toraya, T. et al., "The Synthesis of Several Immobilized Derivatives of Vitamin B12 Coenzyme and Their Use as Affinity Adsorbents for a Study of Interactions of Diol Dehydrase with the Coenzyme." *Journal of Biological'*.

Takahata, Y. et al., Synthesis, Properties and Microbiological Activity of Hydrophobic Derivatives of Vitamin B12. *J. Nutr. Sci. Vitaminol.*, 1995, vol. 14, pp. 515-526.

Kamao, M. et al., "Determination of Plasma Vitamin K by High Performance Liquid Chromatography with Fluorescence Detection Using Vitamin K Analogs as Internal Standards." *J. Of Chromatography B.*, 2005, vol. 816.

Mack, D.O. et al., "The Carboxylation Activity of Vitamin K Analogs with Substitutions at Position 2, 3, or 5." *Journal of Biological Chemistry*, 1979, vol. 254, Apr. 25, pp. 2656-2664.

Mock, D.M. et al., "Urinary Biotin Analogs Increase in Humans During Chronic Supplementation: the Analogs are Biotin Metabolites." *The American Physiological Society*, 1997, pp. 83-85.

International Search Report for PCT/US2002/13890 completed Oct. 28, 2002.

Vesely, D.L. et al., "Biotin Analogs Activate Guanylate Cyclase." *Molecular and Cellular Biochemistry*, 1984, vol. 60, pp. 109-114.

Lambooy, J.P., "Riboflavin Analogs Utilized for Metabolism by a *Lactobacillus Casei Mutant*." Int. J. Biochem., 1984, vol. 16, No. 2, pp. 231-234.

Nielsen, P. et al., "Phosphates of Riboflavin and Riboflavin Analogs: A Reinvestigation by High-Performance Liquid Chromatography." *Analytical Biochemistry*, 1983, vol. 130, pp. 359-368.

Arya, P. et al., "Design and Synthesis of Analogs of Vitamin E: Antiproliferative Activity Against Human Breast Adenocarcinoma Cells." *Bioorganic & Medicinal Chemistry Letters*, 1998, vol. 8, No. 18, pp. 2433-2438.

Trachewsky, D. "Antihypertensive Effect of Riboflavin Analogs in Rats with Mineralocorticoid-Induced Hypertension." Hypertension, 1981, vol. 3, No. 1, Jan-Feb., pp. 75-80.

Skinner, W.A. et al., "Structure-Activity Relations in the Vitamin E Series. II. Derivatives of alpha-Tocopherol Substituted at the 5-Methyl Group." *J Med. Chem.*, 1962, vol. 12, pp. 64-66.

Neuzil, J. et al., "Vitamin E. Analogs: A New Class of Multiple Action Agents with Anti-Neoplastic and Anti-Atherogenic Activity." *Apoptosis*, 2002, vol. 7, pp. 179-187.

Politis, I. et al., " The Effect of Various Vitamin E Derivatives on the Urokinase-Plasmogen Activator System of Ovine Macrophages and Neutrophils." *British Journal of Nutrition*, 2003, vol. 89, pp. 259-265.

Wang, X. et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005, vol. 326.

International PCT Search Report and Written Opinon for PCT Application No. PCT/US2008/064711, completed May 19, 2010.

International PCT Search Report and Written Opinon for PCT Application No. PCT/US2006/037112, completed Nov. 14, 2007.

Reddy J A et al: "Expression and functional characterization of the beta-isoform of the folate receptor on CD34(+) cells," BLOOD, vol. 93, No. 11, Jun. 1,1999, pp. 3940-3948, XP002300805.

Japanese Translation of PCT International Application No. 2005-519078.

Japanese Translation of PCT International Application No. 2004-530678.

Yang et al, Imaging Tumor Folate Receptors using radiolabeled folate and methotrexate, Jour Labelled Compounds and Radiopharmaceuticals, 1999, Sussex, GB, Vol Suppl 1, 42: S696-S697.

Akihiro H. et al., "Affinity for a-tocopherol transfer protein as a determinant of the biological activities of vitamin E analogs." *Federation of European Biochemical Societies*, 1997, vol. 409, pp. 105-108.

Kazui S. et al., "Novel vitamin D3 antipsoriatic antedrugs: 16-En-22-oxa-1a,25-(OH)2D3 analogs," Bioorganic & Medicinal Chemistry, 2006, vol. 14, pp. 1838-1850.

Hisashi T. et al., "c-Fos protein as a target of anti-osteoclastogenic action of vitamin D, and synthesis of new analogs," journal article, *The Journal of Clinical Investigation*, 2006, vol. 116, No. 2, Feb., pp. 528-535.

Masato S. et al., "Synthesis and biological activities of new 1a,25-dihydroxy-19-norvitamin D3 analogs with modifications in both the

(56) References Cited

OTHER PUBLICATIONS

A-ring and the side chain," journal article, *Bioorganic & Medicinal Chemistry*, 2006, 14(12) pp. 4277-94.

Landuer, W. et al., "The Interaction in Teratogenic Activity of the Two Niacin Analogs 3-acetylpyridine and 6-aminonicotinamide," *J Experimental Zoology*, 1962, vol. 151, pp. 253-258.

Nishikawa, Y. et al., "Growth Inhibition of Hepatoma Cells Induced by Vitamin K and Its Analogs." *Journal of Biological Chemistry*, 1995, vol. 270, No. 47, Nov. 24, pp. 28304-28310.

Jallad et al, Dissertation Abstracts International, 2001, 65(5B), p2390.

Stummer et al, J Neurosurg, 2000, 93:1003-1013.

Kennedy et al, Dissertation Abstracts International, 2001, 65(5B), p2354.

Siltsema et al. "Confocal Direct Imaging Raman Microscope: Design and Application in Biology", Applied Spectroscopy, vol. 52, Issue 3, pp. 346-355, 1998.

Sima et at. "Experimental obstructive coronary atherosclerosis in the hyperlipidernic hamster", J. Submicrose Cytol Pathol, vol. 22, No. 1 pp. 1-16, 1990.

Simionescu et at, "Prelesional modifications of the vessel wall in hyperlipidemic atherogenesis: Extracellular accumulation of modified and reassembled lipoproteins.", Ann. NY Arad. Sri., vol. 598. pages 1-16. 1990.

Smart et al., "Protein kinase C activators inhibit receptor-mediated potocytosio by preventing internalization of caveolae", Journal of Cell Biology, vol. 124, No. 8, pp. 307-313, 1994.

Solomin et al.. "Computerized Tomography in Ovarian Cancer", Gynecologic Oncology. vol. 15 pp. 48-56, 1983.

Sudimak et al. "Targeted drug delivery via the folate receptor", Advanced Drug Delivery Reviews, vol. 41, pp. 147-162, 2000.

Sun et al., 'Anhydrous Tetrabutylammonium Fluoride', J. Am. Chem Soc.. vol. 127, No. 7. pages 2050-2051, 2005.

Sun et al., "Room-Temperature Nucleophilic Aromatic Fluorination: Experimental and Theoretical Studies", Angew. Chem. Int. Ed. No. 45, . pp. 2720-2725, 2006.

Becker et at, "Macromolecular Contrast Agents for Optical imaging of Tumors: Comparison of indotricorbocyanine-labeled Human Serum Albumin and Transferrin", Photochemistry and Photobiology, vol. 72, No. 2 , pp. 234-241, May 14, 2000.

Bettio et el, "Synthesis and Preclinicai Evaluetion of a Follic Acid Derivative Labeled with 18F for PET Imaging of Folate Receptor-Positive Tumors". The Journal of Nuclear Medicine, vol. 47, No. 7. pp. 1153-1160, 2006.

Bock et at., "Sulfonamide Structure-Activity Relationships in a Cell-Free System 2 Proof for the Formation of a Sulfonamide-Containing Folate Analog", Journal of Medicinal Chemistry, vol. 17, No. 1, pp. 23-28, 1974.

Boechat et al., "Fluorodenitrations Using Tetramethylammonium Fluoride", J. Soc. Chem. Commun., pp. 921-92, 1993.

Boente et al , "Screening, imaging, and Early Diagnosis of Ovarian Cancer", Clinical Obstetrics and Gynecology, vol. 37, No. 2, pp. 377-391, Jun. 1994.

Bonasera et al., "The Synthesis of [26, 27-11C]Dihydroxyvitarnin D3. a Tracer for Position Emission Tomography (PET), Bioorganic & Medicinal Chemistry", Elsevier Science Ltd., vol. 9, pp. 3123-3128, 2001.

Budinner et at., "New Approaches to Targeting Arthritis with Radiopharmaceuticals", The Journal of Rheumatology, 22;1) Supp. 62.67, 1995.

Burke et al., "Book Review, The Macrophage", British Journal of Cancer, vol. 89 p. 421, 2003.

* cited by examiner

MULTIPHOTON IN VIVO FLOW CYTOMETRY METHOD AND DEVICE

CROSS REFERENCE TO RELATED APPLICATIONS

This application is a U.S. national counterpart application of international application serial no. PCT/US2006/037112 filed Sep. 22, 2006, which claims priority under 35 U.S.C. §119(e) to U.S. Provisional Application Ser. Nos. 60/720,316, filed Sep. 23, 2005, and 60/759,771, filed Jan. 17, 2006, each incorporated herein by reference in its entirety.

GOVERNMENT RIGHTS

This invention was made with United States Government support under Grant No. R01 CA089581, awarded by the National Institutes of Health. The United States Government has certain rights in the invention.

FIELD OF THE INVENTION

This invention relates to an optical method for detecting/quantitating a pathogenic cell population in the bloodstream in vivo and devices therefor. More particularly, ligand-imaging agent conjugates that bind to the cells of the pathogenic cell population are used in an optical method for detecting/quantitating the cell population, and devices for use in this method are described.

BACKGROUND

The presence of pathogenic cells in the bloodstream or the spread of pathogenic cells from other sites to the bloodstream is one of the important factors that determines whether or not a diseased patient will survive. For example, the spread of malignant cells from the primary neoplasm to distant organs is an important factor in determining whether cancer patients will survive. Likewise, the spread of microorganisms to the bloodstream is important in determining whether a patient with an infection will survive. Highly sensitive methods must be developed that can detect and quantitate circulating pathogenic cells, such as metastatic cells, microorganisms, and other types of pathogenic cells in the vasculature at the earliest stages of disease. Achievement of this objective requires probes with selectivity for the pathogenic cells, biocompatibility, and the ability to perform deep tissue imaging.

Flow cytometry is a method that is used for characterizing and quantitating target cell populations using fluorescent probes that render high specificity and low background measurements. However, flow cytometry requires repeated acquisition of samples for examination. Accordingly, the use of this technique for examining the blood of patients is discouraged because of the invasive nature of the sampling that is required. Furthermore, traditional flow cytometry cannot be used for real-time analysis in vivo. Also, the delay between sampling and analysis of the samples may change the host environment so as to cause artificial changes in the samples.

More recently, a conceptual in vivo flow cytometry technique utilizing confocal microscopy has been described for the real-time detection and quantitation of flowing tumor cells in vivo (Georgakoudi, et al. (2004) *Cancer Res.*, 64, 5044-5047; Novak, et al. (2004) *Optics Lett.*, 29, 77-79). However, there is no available method with the requisite sensitivity, biocompatibility, and ability to perform deep tissue imaging for performing the noninvasive detection and quantitation of pathogenic cells in vivo using techniques to label the pathogenic cells in the bloodstream.

SUMMARY

In this application, Applicants describe the noninvasive imaging of flowing pathogenic cells by in vivo flow cytometry. In one embodiment, the noninvasive imaging is achieved by selective in vivo labeling without blood extraction. Multiphoton microscopy (e.g., two-photon), as described herein, can reach vasculature with higher skin penetration depth than confocal microscopy. In one embodiment, Applicants have exploited specific targeting using folate conjugates of high affinity against the folate receptor on cancer cells to achieve tumor selectivity because of the overexpression of the folate receptor on many cancer cells. The methods and devices described herein are applicable to any type of pathogenic cell that flows through the bloodstream as long as the pathogenic cell type expresses a surface receptor that can be used for selective targeting.

In one embodiment, a method is provided for diagnosing disease states mediated by pathogenic cells that can be present in the bloodstream wherein the disease state is diagnosed by detecting a ligand-imaging agent conjugate bound to pathogenic cells and wherein the conjugate is detected using multiphoton in vivo flow cytometry. Ligands that can be used in the conjugates of the present invention include those that bind to receptors expressed on pathogenic cells, such as the folate receptor which is overexpressed on cancer cells or a siderophore receptor or an oligosaccharide receptor expressed on microorganisms.

In another embodiment, a method is provided for diagnosing a disease state mediated by pathogenic cells. The method comprises the steps of administering parenterally to a patient a composition comprising a conjugate or complex of the general formula $A_b$-X where the group $A_b$ comprises a ligand that binds to the pathogenic cells and the group X comprises an imaging agent, and detecting the pathogenic cells that express a receptor for the ligand using mutiphoton in vivo flow cytometry. In another embodiment, $A_b$ comprises a folate receptor binding ligand, or an analog or derivative thereof. In yet another embodiment, $A_b$ comprises other ligands, such as siderophores, or oligosaccharides, that bind to pathogenic cells. In still another embodiment, the imaging agent comprises a chromophore selected from the group consisting of fluorescein, Oregon Green, rhodamine, phycoerythrin, Texas Red, and AlexaFluor 488. In another embodiment, the patient is suffering from a disease state selected from the group consisting of cancer and a disease state mediated by a microorganism.

In another illustrative aspect, $A_b$-X in the method described above is selected from the group consisting of folate-fluorescein, folate-Oregon Green, folate-rhodamine, folate-phycoerythrin, folate-cys-Texas Red, and folate-AlexaFluor.

In yet another embodiment, $A_b$-X in the method described above is selected from the group consisting of desferrioxamine fluorescein and pyoverdine peptide fluorescein.

In another embodiment, a use of a composition is provided wherein the composition comprises a conjugate or complex of the general formula $A_b$-X wherein the group $A_b$ comprises a ligand that binds to pathogenic cells and the group X comprises an imaging agent, in the manufacture of a medicament for diagnosing a disease state mediated by the pathogenic cells wherein the conjugate or complex binds to a receptor expressed on the pathogenic cells and is used to detect the pathogenic cells using mutiphoton in vivo flow cytometry.

In another illustrative aspect, an apparatus for performing multi-photon flow cytometry on a patient into which ligand-imaging agents have been administered is provided. The apparatus comprises a laser array configured to selectively emit light of varying wavelengths, a light conveyance system configured to receive light emitted from the laser array, transmit predetermined wavelengths of light from the laser array to the ligand-imaging agents, receive light emitted by the ligand-imaging agents resulting from exposure to the light from the laser array, and transmit predetermined wavelengths of light emitted by the ligand-imaging agents, and a light processing system configured to receive the predetermined wavelengths of light emitted by the ligand-imaging agents transmitted by the light conveyance system and configured to process the received light to provide an image on a display screen.

BRIEF DESCRIPTION OF THE DRAWINGS

FIG. 6 notations are 1) negative-L1210=cultured leukemia cancer cells L1210, 2.) PU9_FITC__1/100–L1210=PU9–FITC conjugates labeled L1210 cells at a concentration of 1/100, 3.) PU10_FITC__1/100–L1210=PU10–FITC conjugates labeled L1210 cells at a concentration of 1/100, 4.) PU17_FITC__1/100–L1210=PU170–FITC conjugates labeled L1210 cells at a concentration of 1/100, and 5.) EC17–L1210=folate-FITC labeled L1210 cells.

As shown in FIG. 9, the number 1=control sample (no conjugate added), the number 2=non-competed (2 µM conjugate concentration), and the number 3=competed (100-fold excess free desferrioxamine).

As shown in FIG. 10, the number 1=control sample (no conjugate added), the number 2=non-competed (0.1 µM conjugate concentration), and the number 3=competed (100-fold excess free pyoverdine+0.1 µM concentration of pyoverdine peptide). The x-axis indicates fluorescence intensity.

DETAILED DESCRIPTION

Figure 1:
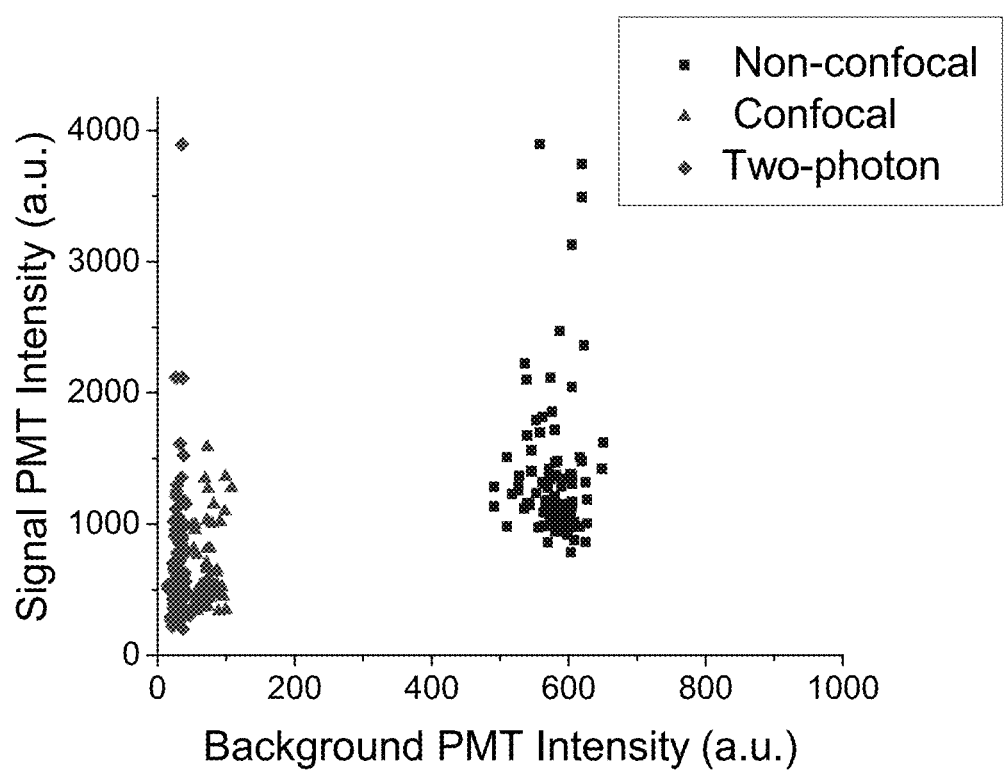
FIG. 1 shows a dot-plot of individual fluorescent $DiIC_{18}(3)$ labeled red blood cells detected in the 152-frame video to demonstrate the comparison of non-confocal, confocal and two-photon microscopy.

Methods are provided for diagnosing disease states mediated (e.g., caused or augmented) by pathogenic cells. Exemplary disease states include cancer and disease states caused by pathogenic microorganisms. Such disease states can be diagnosed by administering parenterally to a patient a composition comprising a conjugate or complex of the general formula $A_b$-X where the group $A_b$ comprises a ligand that binds to the pathogenic cells and the group X comprises an imaging agent, and quantifying or detecting the presence of the pathogenic cells using in vivo multiphoton flow cytometry. The conjugate is typically administered parenterally, but can be delivered by any suitable method of administration (e.g., orally), as a composition comprising the conjugate and a pharmaceutically acceptable carrier therefor. As used herein, "mediated by" in reference to diseases mediated by pathogenic cells means caused by or augmented by.

In one embodiment, the imaging agent (e.g. a reporter molecule) can comprise a chromophore such as, for example, fluorescein, rhodamine, Texas Red, phycoerythrin, Oregon Green, AlexaFluor 488 (Molecular Probes, Eugene, Oreg.), Cy3, Cy5, Cy7, and the like.

Diagnosis typically occurs before treatment. However, in the diagnostic methods described herein, the term "diagnosis" can also mean monitoring of the disease state before, during, or after treatment to determine the progression of the disease state. The monitoring can occur before, during, or after treatment, or combinations thereof, to determine the efficacy of therapy, or to predict future episodes of disease.

The method disclosed herein can be used for both human clinical medicine and veterinary applications. Thus, the patient afflicted with the disease state and in need of diagnosis can be a human, or in the case of veterinary applications, can be a laboratory, agricultural, domestic or wild animal. In embodiments where the conjugates are administered to the patient, the conjugates can be administered parenterally to the patient suffering from the disease state, for example, intradermally, subcutaneously, intramuscularly, intraperitoneally, or intravenously. Alternatively, the conjugates can be administered to the patient by other medically useful procedures.

In the ligand conjugates of the general formula $A_b$-X, the group $A_b$ is a ligand that binds to the pathogenic cells when the conjugates are used to diagnose disease states. Any of a wide number of ligands can be employed. In one embodiment, the ligand conjugates can be used to detect cancer cells and the ligand can be folic acid, a folic acid analog, or another folate receptor-binding molecule. Analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate).

In another embodiment, other vitamins can be used as the ligand for the use of the conjugates in detecting cancer cells. The vitamins that can be used in accordance with the methods described herein include niacin, pantothenic acid, folic acid, riboflavin, thiamine, biotin, vitamin $B_{12}$, vitamins A, D, E and K, other related vitamin molecules, analogs and derivatives thereof, and combinations thereof.

In other embodiments, the ligand can be any ligand that binds to a receptor expressed or overexpressed on pathogenic cells such as microorganisms, including ligands such as siderophores or oligosaccharides.

The ligand can be an oligosaccharide utilized by the pathogenic cells (e.g., microorganisms) for host cell attachment, a siderophore, or a ferrisiderophore complex, or pathogen binding analogs or derivatives thereof, wherein the oligosaccharide, siderophore, or ferrisiderophore complex, or pathogen binding analogs or derivatives thereof, binds to a population of pathogenic cells in vivo that uniquely or preferentially expresses a receptor for the oligosaccharide, siderophore, or ferrisiderophore complex, or pathogen binding analogs or derivatives thereof.

The oligosaccharides for use in accordance with the invention can be any oligosaccharides utilized by pathogenic cells for attachment to the cells of the patient, or analogs or derivatives of these oligosaccharides, suitable for use in binding to pathogenic cells for detection of the pathogenic cells. Such oligosaccharides can be identified by methods such as those described in Scharfman et al., Glycobiol. 9:757-764 (1999), Lingwood, Biopolymers 2:695-700 (1998), and Heildila et al., J. Infect. Disease 176:704-712 (1997).

For a particular type of pathogenic cell, one type of oligosaccharide, or a pathogen binding analog or derivative thereof, can be used or a mixture of oligosaccharides, or pathogen binding analogs or derivatives thereof, can be used depending on the oligosaccharide binding specificity of the pathogenic cell. If a mixture of oligosaccharides, or pathogen binding analogs or derivatives thereof, is used, the oligosaccharides can be oligosaccharides involved in attachment of the pathogenic cells to the cells of the patient. The oligosaccharides can be conjugated to one type of imaging agent or a multiplicity of imaging agents can be used. Additionally, the same oligosaccharides, or a portion thereof, or different oligosaccharides can be used to detect different pathogenic cells depending on the oligosaccharide binding specificities of the different pathogenic cells.

The oligosaccharides, or pathogen binding analogs or derivatives thereof, can be made by any art-recognized procedure such as the procedures described in Preparative Carbohydrate Chemistry, S. Hanessian, Ed., 1997, Marcel Dekker, New York, Basel, Hong Kong, and Monosaccharides, Their Chemistry and Their Roles in Natural Products, P. Collins and R. Ferrier, Eds., 1995, John Wiley & Sons, New York, Brisbane, Toronto, Singapore. Any oligosaccharides implicated in host cell attachment can be used including, but not limited to, sialyl lactose, Lewis glycoconjugates (i.e., Lewis blood group oligosaccharides), sulfatides, gangliotriaosyl, gangliotetraosyl ceramide, sulfogangliotetraosyl ceramide, heparan sulfate, lactosyl ceramide, polyglyocsyl ceramide, asialo-ganglioside $GM_2$, globoside, lacto-N-neotetraose, and sialylated derivatives thereof, and the like.

The siderophores for use in accordance with the invention can be any siderophore or ferrisiderophore complexes, or pathogen binding analogs or derivatives thereof, suitable for use in binding to the pathogenic cells. Thus, siderophores for use in accordance with the invention include both iron-free siderophores and ferrisiderophore complexes. For a particular type of pathogenic cell, one type of siderophore or ferrisiderophore conjugated to an imaging agent can be used, or a mixture of siderophores and/or ferrisiderophore complexes can be used depending on the siderophore/ferrisiderphore binding specificity of the pathogenic cell. If a mixture of siderophores and/or ferrisiderophore complexes is used, the siderophores or ferrisiderophores should bind with high affinity to the pathogenic cells. The siderophores or ferrisiderophores can be conjugated to one type of imaging agent or to a multiplicity of imaging agents. Additionally, the same siderophores/ferrisiderophore complexes or different siderophores/ferrisiderophore complexes can be used to detect different pathogenic cells depending on the binding specificities of the different pathogenic cells for siderophores/ferrisiderophore complexes.

Siderophores are secreted by pathogenic cells and can be purified from the culture medium of the pathogens, and can be complexed with iron, according to art-recognized procedures such as the procedure described in Barnes et al., Biometals 12(1):83-7 (1999), Iijima et al., J. Antibiot. 52(1):20-4 (1999), and Ratledge et al., Microbiology 142(8):2207-12 (1996).

In embodiments where siderophores or oligosaccharides are used as the ligand, the present invention is applicable to such populations of pathogenic cells as bacteria, fungi, including yeasts, viruses, virus-infected cells, mycoplasma, and parasites. Infectious organisms that can be detected with the methods and compositions of the present invention are any art-recognized infectious organisms that cause pathogenesis in a patient, including such organisms as bacteria that are gram-negative or gram-positive cocci or bacilli. For example, *Proteus* species, *Klebsiella* species, *Providencia* species, *Yersinia* species, *Erwinia* species, Enterobacter species, *Salmonella* species, *Serratia* species, *Aerobacter* species, Escherichia species, *Pseudomonas* species, *Shigella* species, *Vibrio* species, Aeromonas species, *Campylobacter* species, *Streptococcus* species, *Staphylococcus* species, *Lactobacillus* species, *Micrococcus* species, *Moraxella* species, *Bacillus* species, *Clostridium* species, *Corynebacterium* species, *Eberthella* species, *Micrococcus* species, *Mycobacterium* species, *Neisseria* species, *Haemophilus* species, *Bacteroides* species, *Listeria* species, *Erysipelothrix* species, *Acinetobacter* species, *Bracella* species, *Pasteurella* species, *Vibrio* species, *Flavobacterium* species, Fusobacterium species, *Streptobacillus* species, *Calymmatobacterium* species, Legionella species, *Treponema* species, *Borrelia* species, *Leptospira* species, Actinomyces species, *Nocardia* species, *Rickettsia* species, and any other bacterial species that causes disease in a patient can be detected with the methods and compositions of the invention.

The binding of the oligosaccharide, siderophore, or ferrisiderophore conjugate, or the oligosaccharide conjugate to the pathogenic cells is directed by a receptor, a transporter, or other surface-presented protein uniquely or preferentially expressed by the pathogenic cells. A surface-presented protein uniquely or preferentially expressed by the pathogenic cells is a receptor not present or present at lower amounts on the cells of the patient providing for selective detection of the pathogenic cells. The binding site for the oligosaccharide, siderophore, or ferrisiderophore complex, or analogs or derivatives thereof, includes surface-presented receptors capable of specifically binding oligosaccharides utilized by pathogenic cells for host cell attachment, or receptors capable of specifically binding siderophores, or ferrisiderophore complexes, or analogs or derivatives thereof.

For conjugates used to detect cancer cells wherein the group $A_b$ is folic acid, a folic acid analog, or another folic acid receptor binding ligand, these conjugates are described in detail in U.S. Pat. No. 5,688,488, the specification of which is incorporated herein by reference. That patent, as well as related U.S. Pat. Nos. 5,416,016 and 5,108,921, each incorporated herein by reference, describe methods and examples for preparing conjugates useful in accordance with the methods described herein. The present imaging agents can be prepared and used following general protocols described in those earlier patents, and by the protocols described herein (for example, in Examples 3 and 11-14).

The conjugates for use in the method described herein can be conjugated by using any art-recognized method forming a complex. This can include covalent, ionic, or hydrogen bonding of the ligand to the imaging agent, either directly or indirectly via a linking group such as a divalent linker. The conjugate is typically formed by covalent bonding of the ligand to the imaging agent through the formation of amide, ester or imino bonds between acid, aldehyde, hydroxy, amino, or hydrazo groups on the respective components of the complex or, for example, by the formation of disulfide bonds.

In one embodiment of the invention where cancer cells are detected, the ligand is folic acid, an analog of folic acid, or any other folate receptor binding molecule, and the folate ligand is conjugated to the imaging agent by a procedure that utilizes trifluoroacetic anhydride to prepare γ-esters of folic acid via a pteroyl azide intermediate. This procedure results in the synthesis of a folate ligand, conjugated to the imaging agent only through the γ-carboxy group of the glutamic acid groups of folate. Alternatively, folic acid analogs can be coupled through the α-carboxy moiety of the glutamic acid group or both the α and γ carboxylic acid entities Illustratively, a variety of folate analogs and derivatives may be substituted for folate itself in forming the folate linker conjugates. Those analogs and derivatives, or protected forms thereof, may be included in the synthetic protocols described herein. For example, folate analogs and derivatives are well-known in the art, such as those described in Westerhof, et al., *Mol. Pharm.* 48: 459-471 (1995), incorporated herein by reference.

In addition, structural modifications of the a linker portion of the conjugates is contemplated herein. For example, a number of amino acid substitutions may be made to the linker portion of the conjugate, including but not limited to naturally occurring amino acids, as well as those available from conventional synthetic methods. In one aspect, beta, gamma, and longer chain amino acids may be used in place of one or more alpha amino acids. In another aspect, the stereochemistry of the chiral centers found in such molecules may be selected to form various mixture of optical purity of the entire molecule, or only of a subset of the chiral centers present. In another aspect, the length of the peptide chain included in the linker may be shortened or lengthened, either by changing the number of amino acids included therein, or by including more or fewer beta, gamma, or longer chain amino acids. In another aspect, the selection of amino acid side chains in the peptide portion may be made to increase or decrease the relative hydrophilicity of the linker portion specifically, or of the overall molecule generally.

Similarly, the length and shape of other chemical fragments of the linkers described herein may be modified. In one aspect, where the linker includes an alkylene chain. The alkylene chain may vary in length, or may include branched groups, or may include a cyclic portion, which may be in line or spiro relative to the allylene chain. In another aspect, where the linker includes a beta thiol releasable fragment, it is appreciated that other intervening groups connecting the thiol end to the hydroxy or carbonate end may be used in place of the ethylene bridge, such as but not limited to optionally substituted benzyl groups, where the hydroxy end is connected at the benzyl carbon and the thiol end is connected through the ortho or para phenyl position, and vice versa.

The conjugates used in accordance with the methods described herein of the formula $A_b$-X are used in one aspect to formulate diagnostic compositions, for administration to a patient, wherein the compositions comprise effective amounts of the conjugate and an acceptable carrier therefor. Typically such compositions are formulated for parenteral use. The amount of the conjugate effective for use in accordance with the methods described herein depends on many parameters, including the nature of the disease being diagnosed, the molecular weight of the conjugate, its route of administration and its distribution, and the possibility of co-usage of other diagnostic agents.

The ligand conjugates are administered in one aspect parenterally and most typically by intraperitoneal injections, subcutaneous injections, intramuscular injections, intravenous injections, intradermal injections, or intrathecal injections. Examples of parenteral dosage forms include aqueous solutions of the conjugate, for example, a solution in isotonic saline, 5% glucose or other well-known pharmaceutically acceptable liquid carriers such as alcohols, glycols, esters and amides. The parenteral compositions for use in accordance with this invention can be in the form of a reconstitutable lyophilizate comprising the one or more doses of the ligand conjugate.

Figure 11:
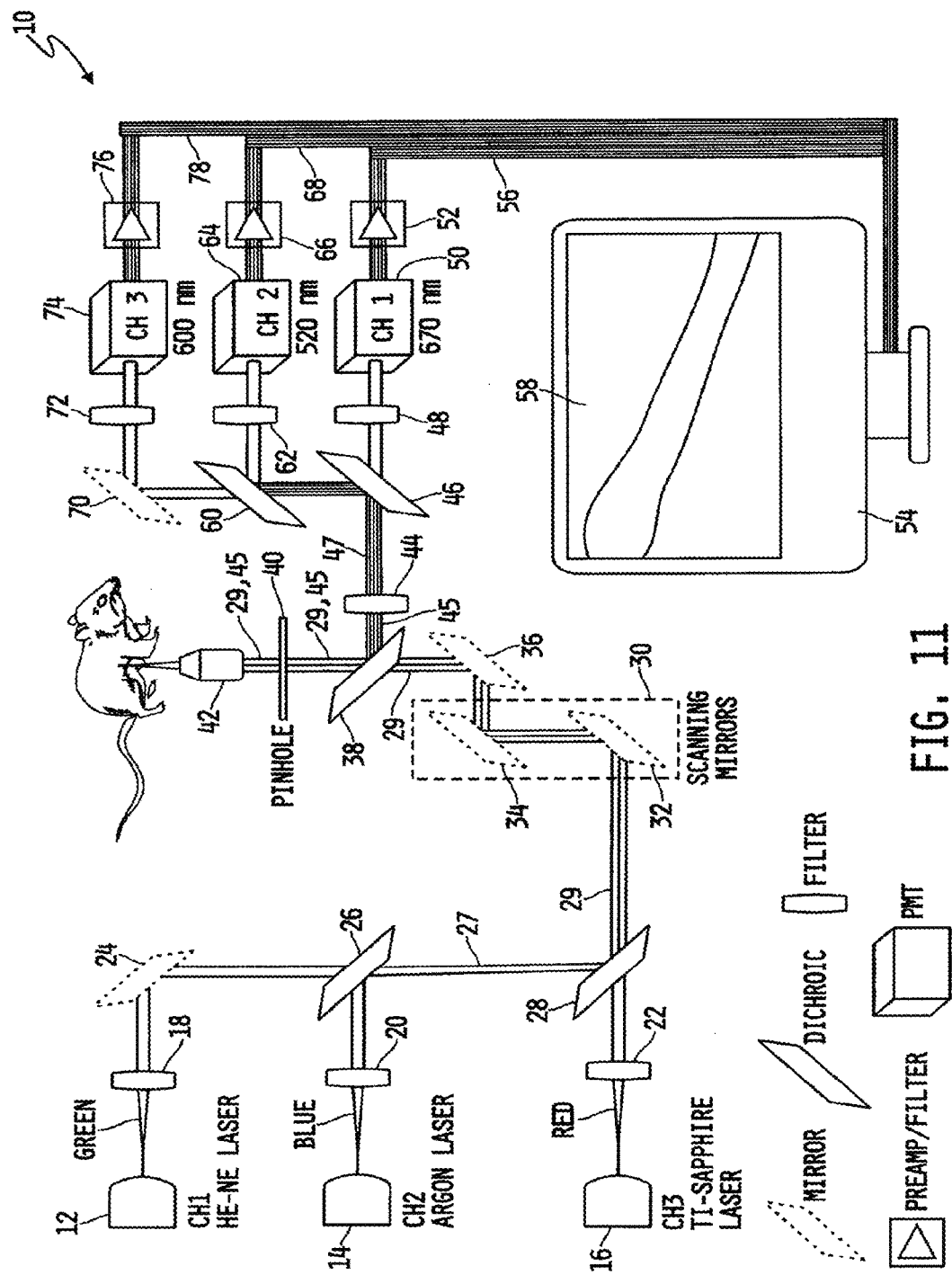
FIG. 11 shows one embodiment of an apparatus for performing an in vivo multi-photon flow cytometry process.

Referring now to FIG. 11, an apparatus 10 for performing an in vivo multi-photon flow cytometry process includes a first laser 12, a second laser 14, and a third laser 16. Illustratively, the first laser 12 is a helium-neon (He—Ne) laser, the second laser 14 is an argon (Ar) laser, and the third laser 16 is a Titanium (Ti)-Sapphire laser. However, in other embodiments, the apparatus 10 may include additional and/or alternative types of lasers. The output laser light beam of the first laser 12, which is illustrated in FIG. 11 by "green" for purposes of clarity, is directed through a first optical filter 18. It should be appreciated the colors associated with various beams is for purposes of clarity and illustration and in no way should limit the scope of this disclosure. The first optical filter 18 is calibrated for use with the first laser 12 and may be configured to transmit a predetermined wavelength or range of wavelengths of light while filtering or blocking light of wavelengths other than the predetermined wavelength or range of wavelengths. For example, in one particular embodiment, the first optical filter 18 is configured to transmit wavelengths of about 543 nanometers and filter other wavelengths. In addition, the first optical filter 18 may be used to reduce the power of the laser light beam produced by the first laser 12.

The output laser light beam of the second laser 14, which is illustrated in FIG. 11 with "blue" for purposes of clarity, is directed through a second optical filter 20. The second optical filter 20 is calibrated for use with the second laser 14 and may be configured to transmit a predetermined wavelength or range of wavelengths of light while filtering or blocking wavelengths other than the predetermined wavelength or range of wavelengths. For example, in one embodiment, the second optical filter 20 may be configured to transmit wavelengths of about 465 nanometers. In another embodiment, the second optical filter 20 may be configured to transmit wavelengths of about 488 nanometers. In a further embodiment, the second optical filter 20 may be configured to transmit wavelengths of about 498 nanometers. Similar to the first optical filter 18, the second optical filter 20 may also be used to reduce the power of the laser beam produced by the second laser 14.

The output laser light beam of the third laser 16, which is illustrated in FIG. 11 with "red" for purposes of clarity, is directed through a third optical filter 22. The third optical filter 22 is calibrated for use with the third laser 16 and may be configured to transmit a predetermined wavelength or range of wavelengths of light while filtering or blocking wavelengths other than the predetermined wavelength or range of wavelengths. For example, in one embodiment, the third optical filter 22 may be configured to transmit wavelengths of about 750 nanometers. In another embodiment, the third optical filter 22 may be configured to transmit wavelengths of about 770 nanometers. As with the first and second optical filters 18, 20, the third optical filter 22 may also be used to reduce the power of the laser beamed produced by the third laser 16.

The apparatus 10 includes a first reflective mirror 24. The first reflective mirror 24 is positioned to reflect the filtered output beam of the first laser 12 through a first dichroic mirror 26. The first dichroic mirror 26 is configured to transmit a predetermined first wavelength or range of wavelengths of light while reflecting a second wavelength or range of wavelengths of light. In the illustrative embodiment, the first dichroic mirror 26 is configured to transmit the wavelengths of the output laser light beam of the first laser 12 and reflect the wavelengths of the output beam of the second laser 14. For example, the first dichroic mirror 26 may be configured to transmit wavelengths of about 543 nanometers while reflecting wavelengths of about 465 nanometers, 488 nanometers, or 498 nanometers depending on the particular second laser 14 used. As such, the first dichroic mirror 26 is positioned such that the filtered output beam of the first laser 12, which is reflected by the first reflective mirror 24, is transmitted through the first dichroic mirror 26 while the filtered output beam of the second laser 14 is reflected by the first dichroic mirror 26. As such, the resulting laser light beam 27 includes wavelengths of the output laser light beam of the first laser 12 and wavelengths of the output laser light beam of the second laser 14.

The light beam 27 is directed to and subsequently reflected by a second dichroic mirror 28. Similar to the first dichroic mirror 26, the second dichroic mirror 28 is configured to transmit a predetermined first wavelength or range of wavelengths of light while reflecting a second wavelength or range of wavelengths of light. In the illustrative embodiment of FIG. 11, the second dichroic mirror 28 is configured to reflect the wavelengths of the light beam 27 (i.e., the wavelengths of the output laser light beams of the first laser 12 and the second laser 14) and transmit the wavelengths of the filtered output laser light beam of the third laser 16. For example, the second dichroic mirror 28 may be configured to reflect light having wavelengths of about 543 nanometers and 465 nanometers (and/or 488 nanometers and 498 nanometers) while transmitting light having wavelengths of about 750 nanometers (or 770 nanometers), depending on the particular second laser 14 and third laser 16 used. The second dichroic mirror 28 is positioned such that the light beam 27 is reflected by the second dichroic mirror 28 while the filtered output beam of the third laser 16 is transmitted through the second dichroic mirror 28. As such, the resulting multi-colored laser light beam 29 includes wavelengths of the output laser light beam of the first laser 12, wavelengths of the output laser light beam of the second laser 14, and wavelengths of the output laser light beam of the third laser 16.

The apparatus 10 also includes a scanning mirror array 30, which is positioned to receive the laser light beam 29 produced by the lasers 12, 14, 16. The scanning mirror array 30 includes a number of reflective mirrors and is configured to direct or control the positioning of the laser light beam 29. In the illustrative embodiment, the scanning mirror array 30 includes a first scanning mirror 32 and a second scanning mirror 34. In some embodiments, one of the scanning mirrors 32, 34 is for X-axis positioning of the laser light while the other scanning mirror 32, 34 is for Y-axis positioning By changing the positioning of the scanning mirrors 32, 34, the position or direction of the laser light beam 29 may be changed. As such, the scanning mirrors 32, 34 may be moved or positioned manually or automatically. For example, in one embodiment, the scanning mirror array 30 includes a number of actuators or motors coupled to the scanning mirrors 32, 34 to move the scanning mirrors 32, 34 in response to control signals. Such control signals may be generated by a control computer or other device configured to control the positioning of the scanning mirrors 32, 34.

The laser light output of the scanning mirror array 30 is subsequently reflected off of a second reflective mirror 36 and through a third dichroic mirror 38. Similar to the first and second dichroic mirrors 26, 28, the third dichroic mirror 38 is configured to transmit a predetermined first wavelength or range of wavelengths of light while reflecting a second wavelength or range of wavelengths of light. In the illustrative embodiment, the third dichroic mirror 38 is configured to transmit the wavelengths of the laser light beam 29, which includes wavelengths of the output laser light beams of the first, second, and third lasers 12, 14, 16. For example, the third dichroic mirror 38 may be configured to transmit wavelengths of about 543 nanometers, 465 nanometers (and/or 488 nanometers and 498 nanometers), and wavelengths of about 750 nanometers (or 770 nanometers), depending on the type of second and third lasers 14, 16, used.

The transmitted multi-colored laser light beam 29 is subsequently directed through a shutter device 40. The shutter device 40 includes a first aperture having an opening large enough such that the laser light beam 29 directed therethrough is not substantially restricted or focused such that non-confocal microscopy may be performed. The shutter 40 also includes a second aperture or pinhole having a smaller opening such that a portion of the laser light beam 29 directed therethrough is restricted or blocked to thereby focus the laser light beam 29 such that confocal microscopy may be performed. As such, the shutter device 40 may be positioned such that the laser light beam 29 travels substantially unrestricted through the first aperture or through the second aperture wherein a portion of the laser light beam 29 is restricted.

The multi-colored laser light beam 29 is subsequently directed into a laser objective 42. The laser objective 42 is operable to further focus the laser light beam 29 onto a desired portion of the experiment subject. For example, in one embodiment, the laser objective 42 is used to focus the laser light beam 29 onto a portion of an ear of a mouse. However, in other embodiments, the laser objective 42 may be used to focus the laser light beam 29 on other portions of the body of the patient such as, for example, a finger of a human subject.

The laser light beam 29 excites the ligand conjugates contained in the blood of the patient. In response to the laser light beam 29, the fluorescent molecules of the ligand conjugates emit a light having a number of different wavelengths via epifluorescence. A portion of the emitted light from the fluorescent molecules is directed through the objective 42 and focused into an emitted light beam 45. The emitted light beam 45 is directed through the shutter 40 and onto the third dichroic mirror 38. The third dichroic mirror 38 is configured to reflect the wavelengths of the light emitted by the fluorescent molecules in response to the laser light beam 29. For example, in one embodiment, the third dichroic mirror 38 is configured to reflect light having wavelengths of about 520 nanometers, 600 nanometers, and 670 nanometers.

The third dichroic mirror 38 reflects the emitted light beam 45 through a fourth optical filter 44. The fourth optical filter 18 is configured to transmit a predetermined wavelength or range of wavelengths of light while filtering or blocking light of wavelengths other than the predetermined wavelength or range of wavelengths. In the illustrative embodiment, the fourth optical filter 18 is configured to transmit the wavelengths of light produced by the fluorescent molecules of the ligand conjugates while reflecting the wavelengths of light of the output laser light beams of the first, second, and third lasers 12, 14, 16. For example, the fourth optical filter 18 may be configured to transmit light having wavelengths of about 520 nanometers, 600 nanometers, and 670 nanometers while reflecting light having wavelengths of about 543 nanometers, 465 nanometers (and/or 488 nanometers and 498 nanometers), and 750 nanometers (or 770 nanometers) depending on the particular second laser 14 and third laser 16 used. Because in operation the third dichroic mirror 38 may reflect some of the laser light produced by the lasers 12, 14, 16, the fourth optical filter 44 is used to filter such laser light from the emitted light beam 45. As such, the fourth optical filter transmits a light beam 47 being formed substantially only from the emitted light of the fluorescent molecules of the ligand conjugates.

The light beam 47 is subsequently directed to a fourth dichroic mirror 46. The fourth dichroic mirror 46 is configured to transmit a predetermined first wavelength or range of wavelengths of light while reflecting a second wavelength or range of wavelengths of light. In the illustrative embodiment, the fourth dichroic mirror 46 is configured to transmit light having a wavelength of about 670 nanometers and reflect light having other wavelengths. The light transmitted by the fourth dichroic mirror 46 is directed onto a fifth optical filter 48. The fifth optical filter 48 is configured to transmit a predetermined wavelength or range of wavelengths of light while filtering or blocking light of wavelengths other than the predetermined wavelength or range of wavelengths. In the illustrative embodiment, the fifth optical filter 48 is configured to transmit light having a wavelength of about 670 nanometers. The filtered light from the fifth optical filter 48 is directed into a first photomultiplier tube (PMT) 50. The first PMT 50 is configured to convert the received light (i.e., light having a wavelength of about 670 nanometers) into an analog signal. However, because the output of the first PMT 50 is a low level signal, a preamplifier and filter block 52 may be used to amplify and filter the output signal of the first PMT 50. The output of the preamplifier and filter block 52 is coupled to a computer system 54 via a number of interconnects 56. The interconnects 56 may be any type of interconnects capable of facilitating electrical communication between the preamplifier and filter block 52 and the computer system 54 such as, for example, wires, cables, printed circuit board traces, fiber optic cables, and the like.

Referring now back to the fourth dichroic mirror 46, the light reflected from the fourth dichroic mirror 46 is directed to a fifth dichroic mirror 60. The fifth dichroic mirror 60 is configured to transmit a predetermined first wavelength or range of wavelengths of light while reflecting a second wavelength or range of wavelengths of light. In the illustrative embodiment, the fifth dichroic mirror 60 is configured to reflect light having a wavelength of about 520 nanometers and transmit light having other wavelengths. The light reflected by the fifth dichroic mirror 50 is directed onto a sixth optical filter 62. The sixth optical filter 62 is configured to transmit a predetermined wavelength or range of wavelengths of light while filtering or blocking light of wavelengths other than the predetermined wavelength or range of wavelengths. In the illustrative embodiment, the sixth optical filter 62 is configured to transmit light having a wavelength of about 520 nanometers. The filtered light from the sixth optical filter 62 is directed into a second photomultiplier tube (PMT) 64. The second PMT 64 is configured to convert the received light (i.e., light having a wavelength of about 520 nanometers) into an analog signal. A preamplifier and filter block 66 is used to amplify and filter the output signal of the second PMT 64. The output of the preamplifier and filter block 66 is coupled to the computer system 54 via a number of interconnects 68. Similar to the interconnects 56, the interconnects 68 may be any type of interconnects capable of facilitating electrical communication between the preamplifier an filter block 66 and the computer system 54 such as, for example, wires, cables, printed circuit board traces, fiber optic cables, and the like.

Referring now back to the fifth dichroic mirror 60, the light transmitted through the fifth dichroic mirror 60 is directed to a third reflective mirror 70. The third reflect mirror 70 reflects the light transmitted through the fifth dichroic mirror 60 onto a seventh optical filter 72. The seventh optical filter 672 is configured to transmit a predetermined wavelength or range of wavelengths of light while filtering or blocking light of wavelengths other than the predetermined wavelength or range of wavelengths. In the illustrative embodiment, the seventh optical filter 72 is configured to transmit light having a wavelength of about 600 nanometers. The filtered light from the seventh optical filter 72 is directed into a third photomultiplier tube (PMT) 74. The third PMT 74 is configured to convert the received light (i.e., light having a wavelength of about 600 nanometers) into an analog signal. A preamplifier and filter block 76 is used to amplify and filter the output signal of the third PMT 74. The output of the preamplifier and filter block 76 is coupled to the computer system 54 via a number of interconnects 78. Similar to the interconnects 56, 68, the interconnects 78 may be any type of interconnects capable of facilitating electrical communication between the preamplifier an filter block 76 and the computer system 54 such as, for example, wires, cables, printed circuit board traces, fiber optic cables, and the like.

The computer system 54 includes an analog-to-digital converter (not shown) for converting the analog signals produced by the blocks 52, 66, 76 into digital signals usable by the computer system 54. The computer system 54 also includes a processor (not shown) configured to process the digital signals into a colored image viewable on a display screen 58 of the computer system 54. Any other suitable apparatus known in the art can be used.

The following examples are illustrative embodiments only and are not intended to be limiting.

EXAMPLE 1

Materials

Fmoc-Lys(Mtt)-Wang resin, Fmoc-Glu-OtBu, HOBT (1-hydroxybenzotriazole) and HBTU (2-(1H-benzotriazole- 1-yl)-1,1,3,3-tetramethyluronium hexafluorophosphate) were purchased from Novabiochem (San Diego). Piperidine, DIPEA (diisopropylethylamine), Rhodamine β isothiocyanate (Rd-ITC) and triisopropyl saline (TIPS) were from Aldrich (Milwaukee). DiIC$_{18}$ (3) and fluorescein isothiocyanate (FITC) were purchased from Molecular Probes (Invitrogen). The PD-10 column (Sephadex G-25M) was from Amersham. EC17 (folate-FITC), rabbit sera, and the folate-binding column were provided by Endocyte, Inc.

EXAMPLE 2

Cell Culture

A leukemia cell line (L1210) from ATCC was cultured in folate-deficient RPMI 1640 (Gibco) for upregulating folate receptor expression. To further improve the ability of L1210 cells to circulate without blocking smaller capillaries, the L1210 cells were sorted using a flow cytometer (Epics® Altra™, Coulter) and the pool of cells smaller than 10 μm was harvested and subcloned. After 10 generations of culturing, these subcloned cells continue to have a relatively smaller size than their presorted counterparts. The leukemia cells were introduced into the blood circulation by tail vein injection.

EXAMPLE 3

Solid Phase Synthesis of Folate Conjugates

The precursor of folate, N$^{10}$-TFA-Pteroic acid was synthesized according to standard procedures. Fmoc-Lys(Mtt)-Wang resin was soaked in DMF for 20 minutes with nitrogen bubbling before the reaction. 20% piperidine was added to cleave the Fmoc protective group. 2.5 e.q. Fmoc-Glu-OtBu, HOBT and HBTU, dissolved in DMF, as well as 4 e.q. DIPEA were added to the reaction funnel. After 2 hours of nitrogen bubbling at room temperature, the Fmoc cleavage step was repeated with 20% piperidine. 1.5 e.q. N$^{10}$-TFA-Pteroic acid and 2.5 e.q. HOBT and HBTU, dissolved in 1:1 DMF/DMSO (dimethylformamide/dimethylsulfoxide), as well as 4 e.q. DIPEA were then added to the reaction for 4 hours with bubbling with nitrogen. The product was then washed with DMF, DCM (dichloromethane), methanol and isopropyl alcohol thoroughly and dried under nitrogen. 1% TFA/DCM (trifluoroacetic acid/dichloromethane) was used to cleave the Mtt (Mtt 4-methyltrityl) group. 2.5 e.q. Rd-ITC, dissolved in DMF, and 4 e.q. DIPEA were added to the resin and reaction was carried out at room temperature overnight under reduced light conditions. Cleavage of the conjugates was achieved by TFA:TIPS:H$_2$O (95:2.5:2.5). The crude product was collected by precipitation with cool ether. The crude product was lyophilized overnight. On the second day, the crude product was hydrolyzed using 10% ammonium hydroxide (pH=10) for 45 minutes with nitrogen bubbling. The product was collected by lyophilization. Purification was carried out using preparative HPLC (Rigel).

EXAMPLE 4

Antibody Purification and Conjugation

Anti-folate receptor polyclonal antibodies PU9, PU10 and PU17 were purified from anti-rabbit serum using a folate affinity column. The samples were desalted using a PD-10 column and then the samples were buffered in PBS (pH 8.0). Conjugation was carried out at a ratio of 80 μg of FITC per mg of antibody at room temperature for 4 hours under reduced light conditions. After conjugation, the labeled antibodies were purified by affinity column chromatography. The samples were desalted using a PD-10 column and then the samples were buffered in PBS (pH=7.4). The antibody concentration and FITC-to-protein ratio were calculated, respectively, as follows using UV/Vis absorbance: C (mg/ml)=[A(280)−0.31*A(495)]/1.4, F/P ratio=3.1*A(495)/[A(280) 0.31*A(495)].

EXAMPLE 5

Animal Model

To perform the IVTPFC (in vivo two-photon flow cytometry) measurement, experiments were carried out on 6-8 week old Balb/c female mice fed a folate-deficient diet for at least 2 weeks. The anesthesia procedure was performed by intraperitoneal injection of avertin (500 mg/kg). The animal to be studied was placed in a chamber with its ear adhered to the bottom of a cover dish with water or glycerol.

EXAMPLE 6

Imaging

In vivo flow cytometry was performed with a laser scanning microscope (IX70/FV300, Olympus Inc.) that permits confocal, non-confocal, and two-photon excitation fluorescence (TPEF) imaging. A 543-nm He—Ne Laser was used for non-confocal and confocal fluorescence imaging with output power of 1 mW out of the objective. A femtosecond Ti-sapphire laser (Mira900, Coherent Inc.) was used for TPEF with an output power of 35 mW out of the objective. The pulse duration is 100 fs at 800 nm and the repetition rate is 77 MHz. For probing deep blood vessels, a 40×IR water objective (Olympus Inc.) with a working distance of 3.3 mm and numerical aperture (N.A.) of 0.8 was used to focus the pulse laser beam onto the ear surface. Data were acquired either by two-dimensional XY scanning or by one dimensional scanning along a line traversing the blood vessel.

EXAMPLE 7

Ex Vivo Labeling of Red Blood Cells

Blood collected from anesthetized mice by paraorbital extraction was suspended in either 3.8% citrate or 40 U/ml of sodium heparin at 10% hematocrit (hct). Red blood cells (RBCs) were separated from platelet-rich plasma by centrifugation (200×g, 10 minutes, room temperature (RT)) and washed three times (200×g, 10 minutes, RT) with CGS buffer and finally resuspended in PBS at a 20% hct. Labeling of RBCs with DiIC$_{18}$(3) (2.5 mg/ml, DMSO) was performed by adding the dyes to the cells at a final concentration of 25 μg/ml, followed by inversion for 30 seconds. RBCs were pelleted by centrifugation and again resuspended at 20% hct in PBS. The labeling was repeated and washing was done as above and the RBCs were resuspended in PBS at a 50% hct for injection.

EXAMPLE 8

In Vivo Labeling of Tumor Cells

The L1210 cells were introduced into the blood circulation by intravenous injection through the tail vein. After the inoculation of L1210 cells, 3 nmole (150 nmole/kg) of folate-rhodamine was injected through the other tail vein using three doses of 1 nmole folate-rhodamine each every 5 minutes.

EXAMPLE 9

Rage Processing and Quantitation

The digitized signal collected from line scanning was exported into a 2D array and analyzed by the software—IVFlow developed on the MATLAB 7.0 platform. The high frequency noise was filtered with a moving window. The width of the window corresponds to the diameter of targeted cells. Two times the background fluorescence was set as a gate value to remove any pseudosignals caused by pixel noise. The number of fluorescent peaks along with the height of each peak was then determined simultaneously.

EXAMPLE 10

Evaluation of Non-Confocal, Confocal, and Two-Photon Microscopy for In Vivo Flow Cytometry Three optical imaging methods were performed on the same blood vessel. Red blood cells were fluorescently labeled with $DiIC_{18}$ (3) and were detected in flowing blood circulation by video acquisition. The signal and background fluorescence intensities were characterized by the processing of digitized signals from individual fluorescent cells. FIG. 1 shows the dot-plot of both signal and background intensity profiles of individual fluorescently labeled red blood cells. Table 1 below (see Example 15) summarizes the signal-to-background ratio as well as the detection sensitivity of the three optical imaging methods. The data indicate that confocal microscopy is almost half as sensitive as the other two imaging methods because of the tightly focusing plane in the z-axis. Consequently, compared to non-confocal and confocal microscopy, TPEF presents extremely low background without losing any sensitivity. The TPEF excitation has higher skin penetration depth and less photon-damage to biological samples than one-photon excitation due to less scattering and absorption. Based upon the model study by using red blood cells, TPEF is the best among these three types of imaging to apply to in vivo flow cytometry.

EXAMPLE 11

Synthesis of Folate-Cys-Texas Red

Texas Red $C_2$-maleimide (Molecular Probes, Eugene, Oreg.) was dissolved in dimethyl sulfoxide (DMSO) (1 mg in 200 μl DMSO). A 1.4 molar equivalent (1 mg) of Folate-Cys was added to the solution and mixed for 4 hours at room temperature. Folate-Cys-Texas Red (Folate-Texas Red) was purified by reverse-phase HPLC on a C18 column at a flow rate of 1 ml/min. The mobile phase, consisting of 10 mM $NH_4HCO_3$ buffer, pH 7.0 (eluent A) and acetonitrile (eluent B), was maintained at a 99:1 A:B ratio for the first five minutes and then changed to 70:30 A:B in a linear gradient over the next 30 minutes followed by a 1:99 A:B linear gradient over the last 15 minutes. Folate-Cys-Texas Red eluted as two isomer peaks at 44.5 and 45.8 minutes. The product was confirmed by mass spectroscopy and the biologic activity was confirmed by fluorescence measurement of its binding to cell surface folate receptors on folate receptor positive M109 cells in culture.

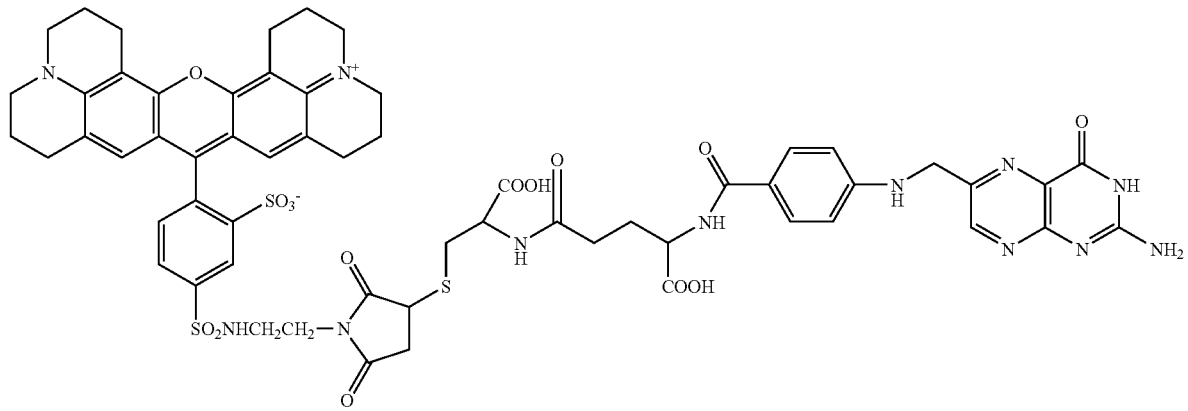

Texas Red - Cys--γ-Glu-Pteroic Acid
MW 1273.37

EXAMPLE 12

Synthesis of Folate-Oregon Green 514

Standard Fmoc peptide chemistry was used to synthesize a folate peptide linked to Oregon Green (Molecular Probes, Eugene, Oreg.) attached to the γ-COOH of folic acid. The sequence Lys-Glu-Pteroic acid (Folate-Cys) was constructed by Fmoc chemistry with HBTU and N-hydroxybenzotriazole as the activating agents along with diisopropyethylamine as the base and 20% piperidine in dimethylformamide (DMF) for deprotection of the Fmoc groups. An α-t-Boc-protected N-α-Fmoc-L-glutamic acid followed by a $N^{10}$-trifluoroacetylpteroic acid was linked to a Fmoc-protected lysine wang resin containing a 4-methyltrityl protecting group on the E-amine. The methoxytrityl protecting group on the ε-amine of lysine was removed with 1% trifluoroacetic acid in dichloromethane to allow attachment of Oregon Green (Folate-Oregon Green). A 1.5 molar equivalent of Oregon Green carboxylic acid, succinimidyl ester was reacted overnight with the peptide and then washed thoroughly from the peptide resin beads. The Folate-Oregon Green was then cleaved from the resin with a 95% trifluoroacetic acid-2.5% water-2.5% triisopropylsilane solution. Diethyl ether was used to precipitate the product, and the precipitant was collected by centrifugation. The product was washed twice with diethyl ether and dried under vacuum overnight. To remove the $N^{10}$-trifluoracetyl protecting group, the product was dissolved in a 10% ammonium hydroxide solution and stirred for 30 minutes at room temperature. The product was precipitated with combined isopropanol and ether, and the precipitant was collected by centrifugation.

CBS), pH 7.4. The solution was allowed to react overnight at 4° C. and the labeled protein (Mr~260 kDa) was purified by gel filtration chromatography using a G-15 desalting column. The folate labeling was confirmed by fluorescence microscopy of M109 cells incubated with folate-phycoerythrin in the presence and absence of 100-fold excess of folic acid. After a 1-hour incubation and 3 cell washes with PBS, the treated cells were intensely fluorescent, while the sample in the presence of excess folic acid showed little cellular fluorescence.

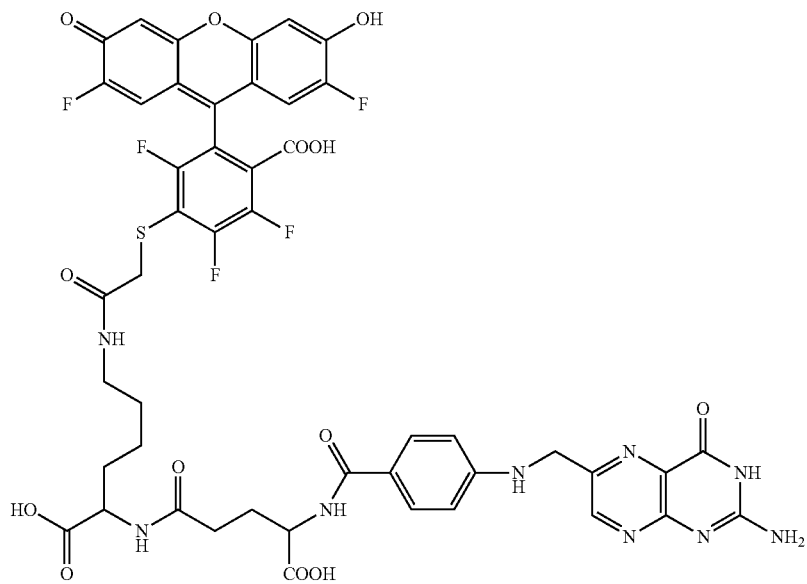 [SMILES: Nc1nc2ncc(CNc3ccc(C(=O)NC(CCC(=O)NC(CCCCNC(=O)CSc4c(F)c(F)c(C(=O)O)c(-c5c6cc(F)c(=O)cc-6oc6cc(O)c(F)cc56)c4F)C(=O)O)C(=O)O)cc3)nc2c(=O)[nH]1]

EXAMPLE 13

Synthesis of Folate-R-Phycoerythrin

Folate-phycoerythrin was synthesized by following a procedure published by Kennedy M. D. et al. in *Pharmaceutical Research*, Vol. 20(5); 2003. Briefly, a 10-fold excess of folate-cysteine was added to a solution of R-phycoerythrin pyridyldisulfide (Sigma, St. Louis, Mo.) in phosphate buffered saline

EXAMPLE 14

Synthesis of Folate-Fluorescein

Folate-FITC was synthesized as described by Kennedy, M. D. et al. in *Pharmaceutical Research*, Vol. 20(5); 2003.

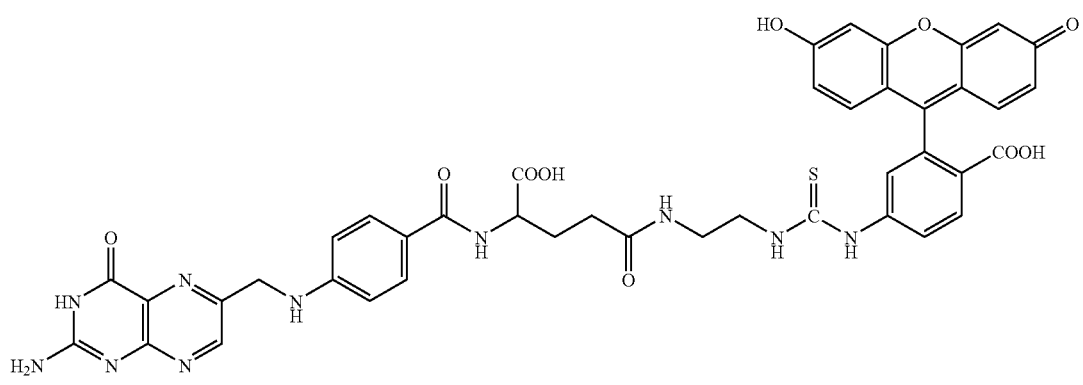

Folate-EDA-FITC
MW 888.90

EXAMPLE 15

In Vivo Folate-Rhodamine Conjugate Blood Clearance

Figure 2:
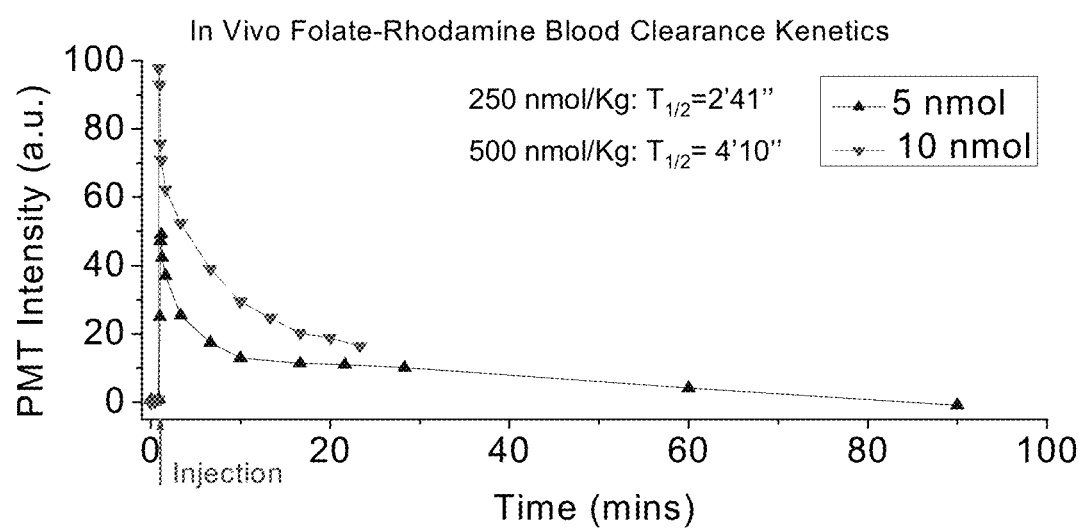
FIG. 2 shows in vivo folate-rhodamine blood clearance kinetics. An arrow marks the injection time point. The symbols show depletion with administration of two different doses of folate-rhodamine. Time series is in the xy-plane over a period of 30 minutes were recorded with one picture every five seconds. Blood vessel fluorescence was quantified with the profile function in each series by calculating the statistical mean average using FlowView software 4.3.

Applicants investigated the in vivo clearance kinetics of folate-rhodamine by performing in vivo TPEF imaging. As shown in FIG. 2, the half-lives of folate-rhodamine from blood circulation at different injection doses within FDA approval limits are shorter than 5 minutes. The retained 10% folate-rhodamine may be attributed to the binding of the probes to serum proteins. The background studies show that the peak intensity at the dose of 500 nmol/kg is two-fold relative to the 250 nmol/kg dose. The curves also illustrate that the background decreased to 10% of the peak intensity in about 10-15 minutes. Consequently, the background caused by in vivo labeling using folate conjugates would not interfere with the fluorescent signals emitted from the target cells.

Comparison of non-confocal, confocal and two-photon microscopy for in vivo sensing $DiIC_{18}(3)$ labeled red blood cells is shown in Table 1 below. The excitation wavelength for non-cofocal and confocal fluorescence microscopy is 543 nm. The excitation wavelength of two-photon fluorescence microscopy is 730 nm. All statistical results are based upon a 152-frame video. The signal or background fluorescence intensity and signal-to-background (S/B) ratio are quantified and calculated with the profile function by FlowView software 4.3.

TABLE 1

|  | Non-confocal | Confocal | Multiphoton |
| --- | --- | --- | --- |
| Output Power | 1 mW | 1 mW | 35 mW |
| Background Intensity (a.u.) | 491.6-650.5 | 46.63-108.0 | 14.65-46.60 |
| Signal Intensity (a.u.) | 785.9-3895 | 336.5-1587.5 | 204.0-3895 |
| S/B Ratio | 1.30-6.98 | 8.00-62.37 | 5.51-108.90 |
| S/B Mean | 2.36 | 9.37 | 22.38 |
| Number of Detected Cells/min | 100 | 55 | 107 |

EXAMPLE 16

In Vivo Labeling and Imaging of Target Tumor Cells

Figure 3:
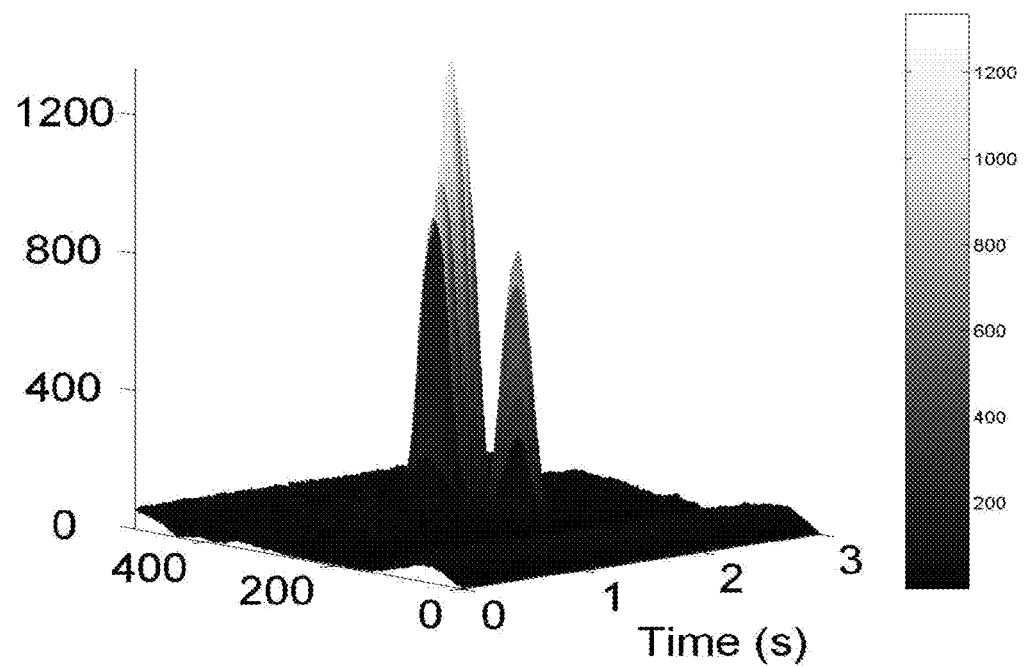
FIG. 3 shows a 3D demonstration of a digitized signal from one dimensional line scanning processed by software developed on MATLAB 7.0 platform. A 50-point average algorithm is used to eliminate the high-frequency noise.
Figure 4:
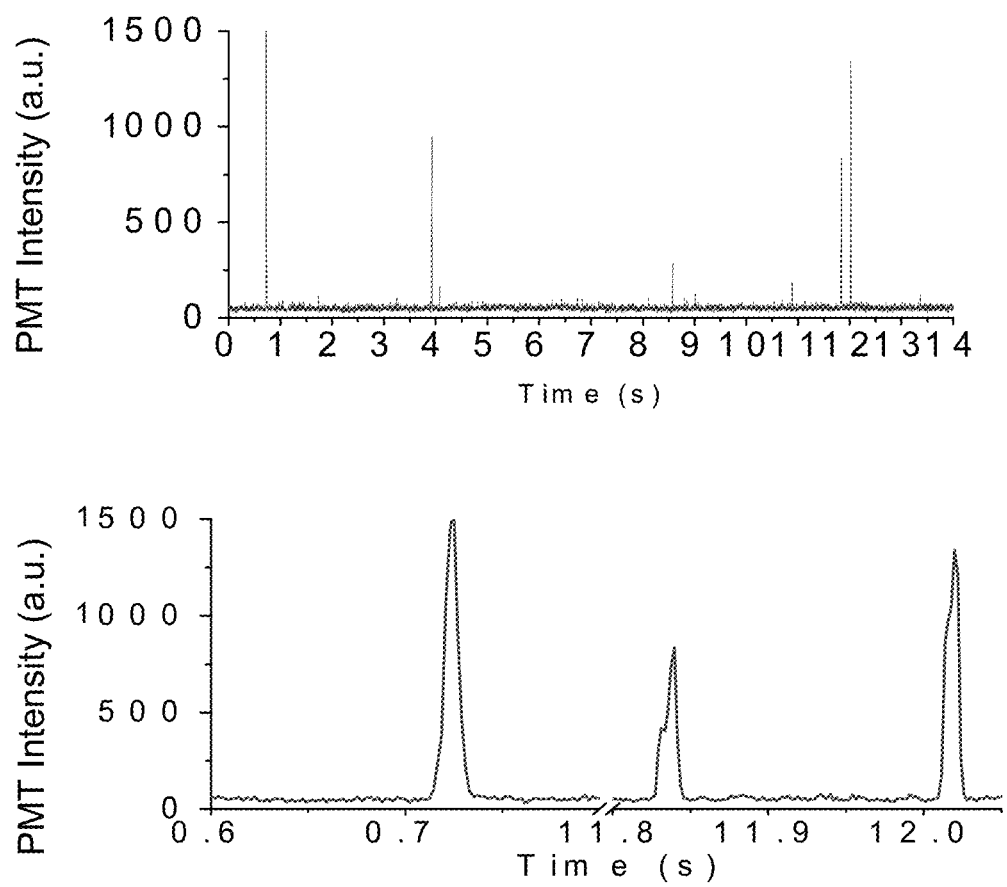
FIG. 4 shows digitized signals from in vivo flow cytometry processed by software developed on MATLAB 7.0 platform. A 50-point average algorithm is used to eliminate the high-frequency noise. The background (about 100) from blood before injection is subtracted.
Figure 5:
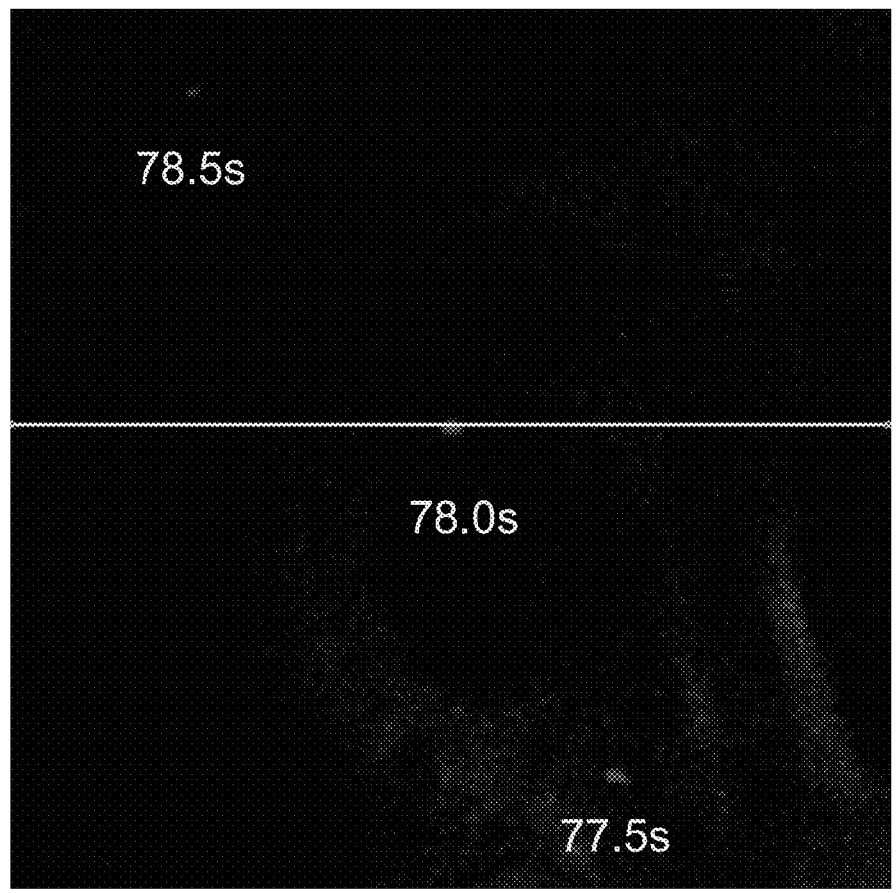
FIG. 5 shows a combined image of three consecutive frames, spanning 1 second, from a movie acquired at 2 frames/second showing in vivo a folate-rhodamine labeled L1210 cell traveling through a blood vessel. One cell is marked by different time points as it is imaged at 77.5 seconds, 78.0 seconds, and 78.5 seconds, respectively.
Figure 5:
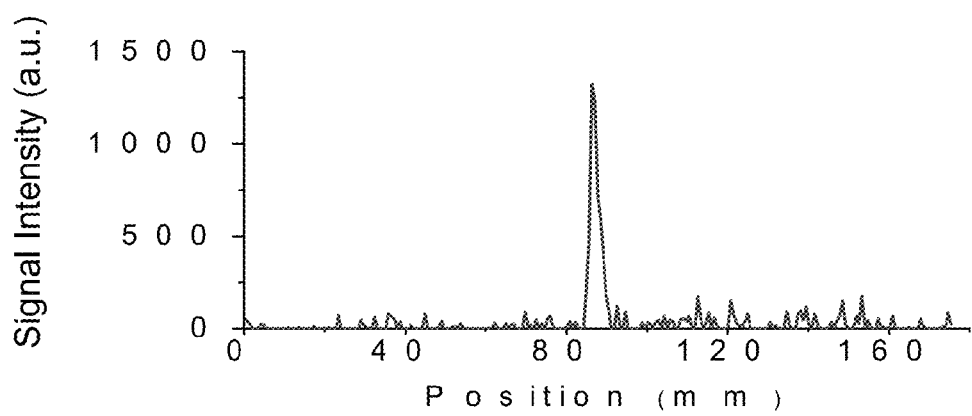

In vivo labeling of target tumor cells was carried out by the injection of folate-rhodamine conjugates. To achieve a faster scanning rate, one dimensional line scanning across a single blood vessel at the rate of 250 frames per second (f/s) was used to acquire the signals from the folate-rhodamine labeled tumor cells. As shown in FIG. 3, the digitized signals first were exported and transformed by MATLAB to a three dimensional pattern with definitions of both timing and intensity. IVFlow software developed on a MATLAB platform then removed the high-frequency noise by point average algorithm (FIG. 4). The velocity of flowing cells was derived from the full width at the half maximum (FWHM) of the peaks. The velocity, calculated from the digitized signals, ranges from 1 mm/second to 3 mm/second and is consistent with previous studies. In FIG. 5, an example of a single fluorescent cell traveling in the blood vessel was demonstrated by combining three consecutive frames from a video at different time points. At the same time, the intensity profile was drawn along the yellow line for the middle frame to illustrate the signal intensity and background.

EXAMPLE 17

Comparison of Antibody Conjugates and Folate Conjugates

Three polyclonal antibodies (described in Example 4 above; PU9, PU10, and PU17) from anti-rabbit sera against the folate receptor were conjugated with fluorescein isothiocyanate (FITC) and tested by in vivo flow cytometry. However, there were no signals captured by our fast line scanning even at rate of 1000 f/s. The reason could be lower labeling efficiency of relatively bulky antibodies or fast depletion of the tumor cells triggered by the immuno-phagocytosis by macrophages or both.

Figure 6:
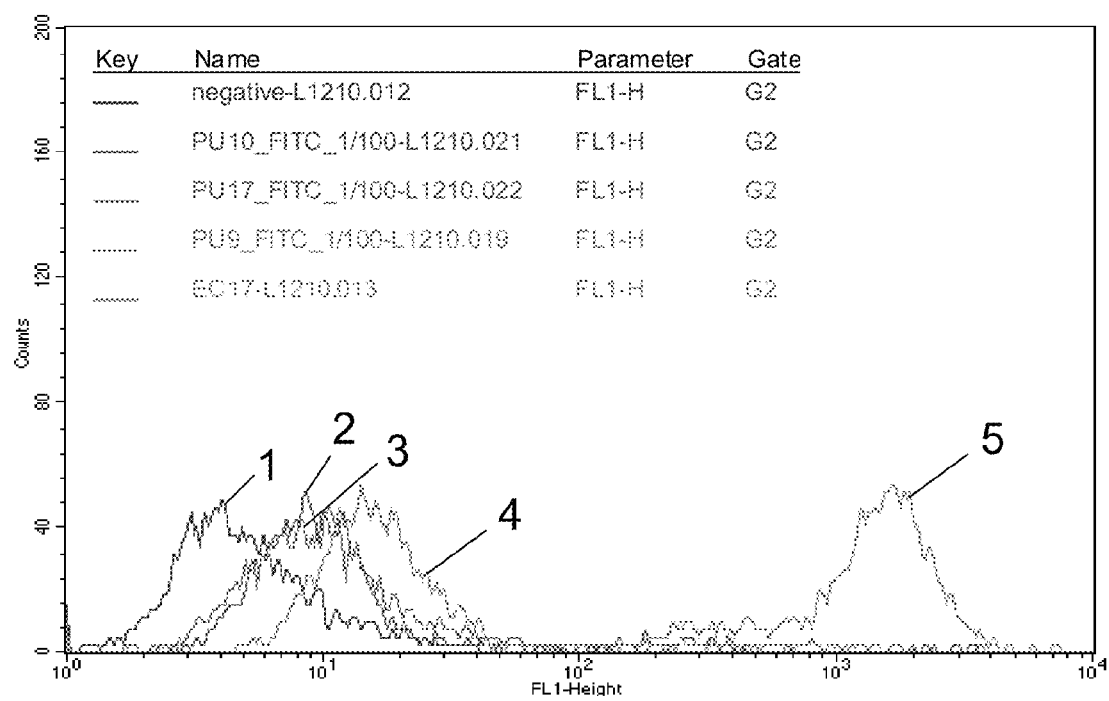
FIG. 6 shows FACS data showing the comparison between antibody conjugates and folate conjugates. Labeling was carried out by incubating L1210 cells with 1 mg/ml of antibody conjugates or 50 nM folate-FITC (EC17) for 30 minutes. The cell culture was then washed three times with PBS.

Further, an ex vivo affinity binding assay on cultured cells by FACS (Fluorescence-Activated Cell Sorter) indicates that the labeling (i.e., binding) efficiency of the three antibodies is about 10-fold lower than for folate-FITC (EC17; FIG. 6). Cultured L1210 cells were incubated, respectively, with folate-FITC (50 nM) and separately with the three antibody-FITC conjugates (1:100, 1 mg/ml) at 37° C. for 30 minutes. The weaker binding of the antibody may be due to the spatial hindrance caused by bulky hydration volume compared to the small ligand conjugates. This may mainly account for the failure of in vivo labeling using antibody conjugates.

EXAMPLE 18

FACS Assay for Cultured Kb Cells in Blood

Cultured KB cells were labeled by DiD (Molecular Probes, Oreg.), a lipophilic dye that non-specifically stains the cell membrane. After incubation with DiD at a concentration of 1:200 at 37° C. for 20 minutes, the cells were digested and washed using physiological buffer (PBS) three times to wash away the remaining DiD in the incubation medium. The DiD-labeled KB cells were then added to 1 ml of whole blood from normal subjects (human) at different numbers varying from $10\text{-}10^6$. Folate-bodipy, an analog of folate-FITC but resistant to pH cleavage, was added to the prepared blood samples at a concentration of 50 nM. FACS assays were performed to investigate the recovery ratio and detection limit of the ex vivo flow cytometer. 500 µl of blood was spiked into the flow cytometer. Control groups were used to determine the gates of correct size and compensation for the crosstalk between two channels as follows:

a.) whole blood;
b.) cultured KB cells;
c.) DiD labeled KB cells;
d.) folate-bodipy labeled KB cells;
e.) both DiD and folate-bodipy labeled KB cells.

Table 2 notation is 1.) All=all DiD positive detected in 500 µl blood samples, 2.) DiD+=number of DiD positive cells appearing within gate of correct size ($N_D$) of KB cells, 3.) Fol-Bp+=number of both DiD and folate-bodipy positive cells within gate of the correct size ($N_{DF}$).

$$\text{Recovery}(\%) = N_D/N_{DF}$$

TABLE 2

|  | 10 | $10^2$ | $10^3$ | $10^4$ | $10^5$ | $10^6$ |
| --- | --- | --- | --- | --- | --- | --- |
| All | 3 | 26 | 301 | 4411 | 39877 | 259270 |
| DiD + | 1 | 22 | 251 | 3762 | 33282 | 217017 |
| Fol-Bp+ | 0 | 14 | 206 | 3386 | 30740 | 205972 |
| Recovery (%) | 0 | 63.6 | 82.1 | 90.0 | 92.4 | 94.9 |

EXAMPLE 19

Materials for Examples 20-27

Desferrioxamine mesylate, fluorescein isothiocyanate, triethylamine, preparative silica gel 60 plates, analytical silica gel 60 plates, diisopropylethylamine (DIPEA), trifluoroacetic acid (TFA), piperadine, dimethylformamide (DMF), PD10 (G25) columns, G50 Sephadex, nutrient agar, nutrient broth, Luria broth, Luria agar, dipyridyl, dimethyl sulfoxide (DMSO) octadecylsilane packing, and CM-Sephadex were purchased from Sigma-Aldrich (St. Louis, Mo.). *Pseudomonas aeruginosa* ATCC 15692 and *Yersinia enterocolitica* ATCC 51871 were purchased from the American Type Culture Collection (Manassas, Va.). EDC(1-Ethyl-3-[3-dimethylaminopropyl]carbodiimide Hydrochloride) was purchased from Pierce (Rockford, Ill.). All solid phase synthesis reagents were purchased from NovaBiochem (Switzerland).

EXAMPLE 20

Preparation of Desferrioxamine Fluorescein

Forty milligrams (0.061 mMoles) of desferrioxamine mesylate (to form a siderophore conjugate) was reacted with 71 milligrams of fluorescein isothiocyanate (0.182 mMoles) and 40 µL's triethylamine in 1 mL of dry dimethyl sulfoxide (DMSO) for 6 hours in the dark. Upon completion, the reaction mixture was added to 10 mL's of rapidly stirring diethyl ether to remove the DMSO. Three more 10 mL additions of diethyl ether were employed to remove the bulk of the DMSO. Each successive addition was decanted from the crude reaction mixture and the final crude product dried under vacuum and re-suspended in 2 mL's of 85:15 chloroform/methanol. This mixture was streaked onto a preparative silica gel 60 plate and developed for 1 hour with 85:15 chloroform/methanol as the mobile phase. The product band was carefully scraped from the preparative silica gel plate, ground using a mortar and pestle, placed on a whatman #1 filter and washed from the silica gel with methanol. Methanol was removed by vacuum and the product characterized by analytical TLC and MALDI-TOF mass spectrometry.

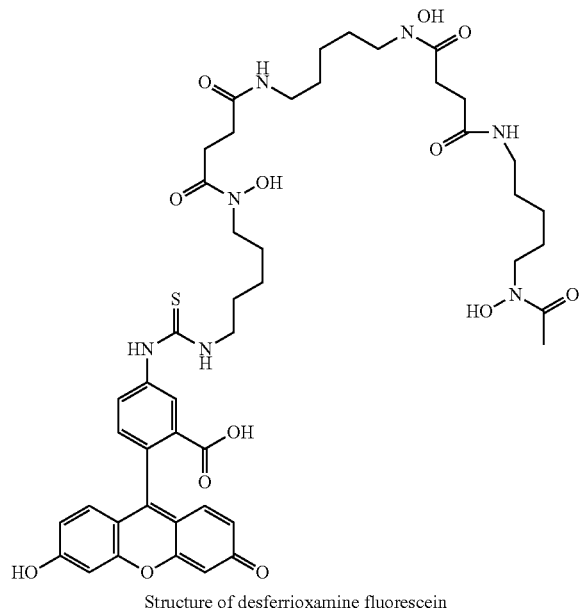

Structure of desferrioxamine fluorescein

EXAMPLE 21

Purification of Pyoverdine PaA

Pyoverdine from *Pseudomonas aeruginosa* PAO1 (ATCC 15692) was purified according to Albrecht-Gary, et al., *Inorg. Chem.* 33: 6391-6402 (1994). Four, two liter conical flasks containing 1 liter of culture media, were inoculated with bacteria previously streaked on nutrient agar plates (cultured for 24 hours at 28° C.) and grown for 48 hours at 28° C. with mechanical agitation of 220 rpm in a dry air incubator/shaler. The culture media consisted of: 6 g $K_2HPO_4$, 3 g $KH_2PO4$, 1 g $(NH_4)_2SO_4$, 0.2 g $MgSO_4$ $7H_2O$, and 4 g succinic acid per liter. The media was adjusted to pH 7.0 with 1 M NaOH prior to sterilization. All glassware was exhaustively rinsed with 3 M HCl followed by distilled water to prevent contamination with iron. Following the 48 incubation period, the 4 L's of culture media were centrifuged at 20,000×g for 30 minutes, acidified to pH 4.0 by addition of formic acid to the culture media, and ultra filtered through a 0.45 µm membrane. The filtered media containing the crude siderophores was applied to an octadecylsilane column (l=15 cm i.d.=2.5 cm) at a flow rate of 2 mL/min using a Pharmacia LKB series 500 FPLC pump. The column was washed with 0.5 L's of a pH 4.0 aqueous solution of acetic acid to remove the inorganic media salts and the crude siderophores were eluted from the C18 column using 1:1 acetonitrile/0.05 M pH 5.0 pyridine acetate buffer (0.5 L's). All solvents were evaporated using a rotary evaporator. Two hundred fifty milligrams of crude siderophores were dissolved in 5 mL of 0.05 M pyridine acetate buffer (pH 5.0) and applied to a CM-Sephadex C-25 ion-exchange column (l=15 cm, i.d.=2.5 cm) equilibrated with 5-6 column volumes of the same buffer. The siderophores were eluted isocratically with 0.05 M pyridine-acetic acid buffer pH 5.0 (0.3 L), then with a linear gradient of the same buffer (0.05-2 M; 2×1 L). Ten milliliter fractions were collected with Pharmacia LKB fraction collector. Two hundred microliter aliquots were removed from each fraction and applied to a 96 well microplate and read at 380 nm using a VersaMax microplate reader (molecular Devices, Sunnyvale, Calif.). Appropriate fractions were combined and evaporated. Two main siderophores (PaA and PaB) were isolated. Identity of PaA was confirmed by MALDI-TOF mass spectrometry using a Perceptive Biosystems Voyager mass spectrometer.

EXAMPLE 22

Preparation of Pyoverdine Peptide Fluorescein

Pyoverdine peptide fluorescein (a siderophore conjugate) was prepared by constructing a peptide scaffold (Gly-Lys-Glu) via standard FMOC peptide synthesis and selectively deprotecting the lysine side chain by the addition of 4-5 mL's of 1% TFA in DCM X2 and reacting for 5 minutes. Deprotection was confirmed by a positive Kaiser test. Fluorescein isothiocyanate was reacted with the deprotected lysine side chain; whereas, pyoverdine was coupled to the n-terminal glutamic acid. Each step was monitored via Kaiser test analysis (free amine) with all steps yielding consistent coupling results. MALDI-TOF mass spectrometry analysis was performed on the crude product with three peaks corresponding to the product (m/z=2054), pyoverdine (m/z)=1334), and a cleaved peptide fluorescein (2 $Na^+$ adduct; m/z=764) fragment. The structure of pyoverdine peptide fluorescein is shown below.

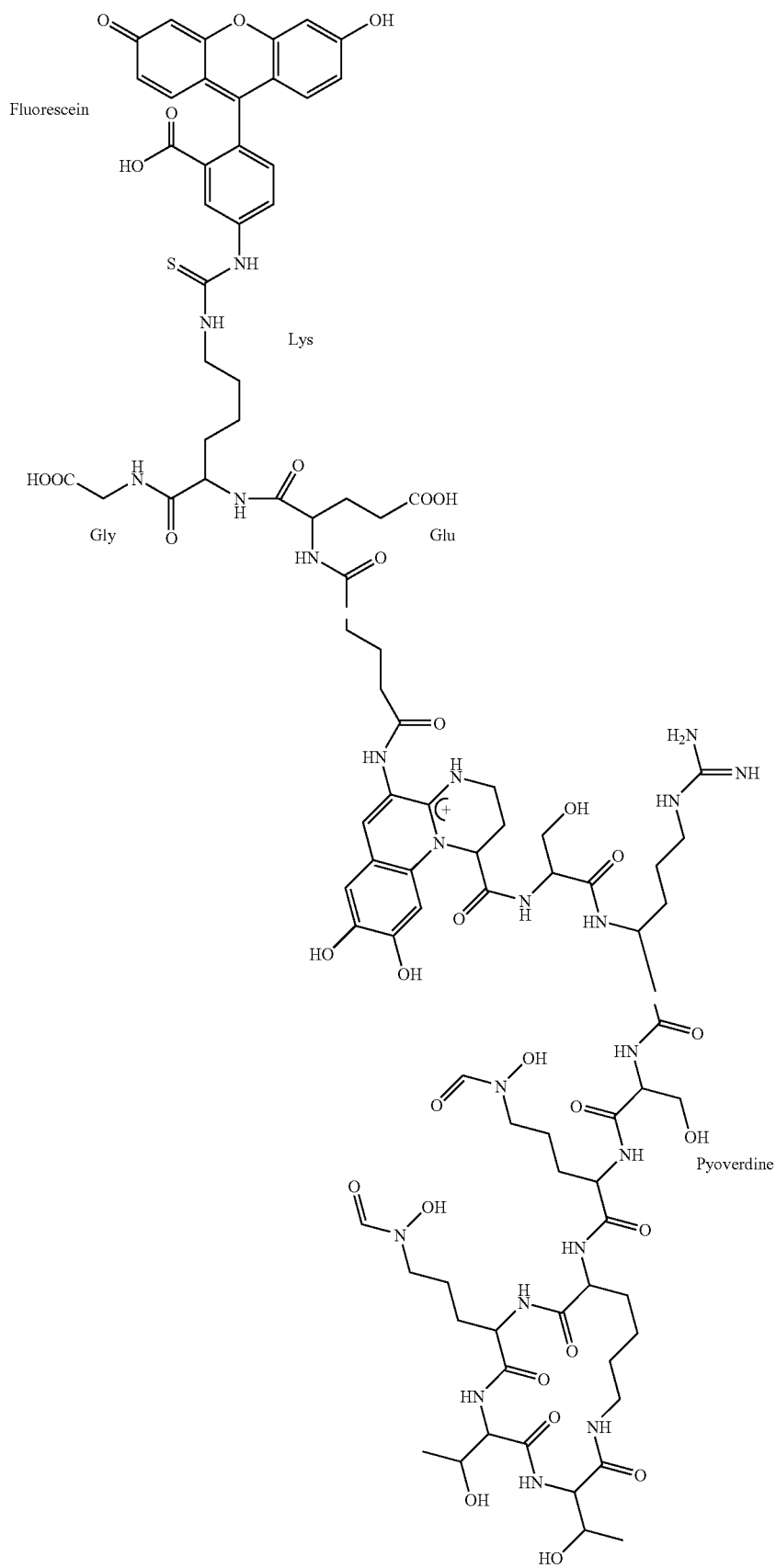 [SMILES: CC(O)C1NC(=O)C(CCCN(O)C=O)NC(=O)C(NC(=O)C(CCCN(O)C=O)NC(=O)C(CO)NC(=O)C(CCCNC(=N)N)NC(=O)C(CO)NC(=O)C2CCN[c+]3c(NC(=O)CCCC(=O)NC(CCC(=O)O)C(=O)NC(CCCCNC(=S)Nc4ccc(-c5c6ccc(=O)cc-6oc6cc(O)ccc56)c(C(=O)O)c4)C(=O)NCC(=O)O)cc4cc(O)c(O)cc4n32)CCCCNC(=O)C(C(C)O)NC1=O]

EXAMPLE 23

Maintenance of Bacterial Strains

This procedure applies to Examples 25-26. *Pseudomonas aeruginosa* and *Yersinia enterocolitica* were maintained at −80° C. in a glycerol stock solution consisting of 15% glycerol and nutrient broth (*Pseudomonas aeruginosa*) or Luria broth (*Yersinia enterocolitica*). Subcultures were maintained on nutrient agar plates (*Pseudomonas aeruginosa*) and Luria agar plates (*Yersinia enterocolitica*).

EXAMPLE 24

Fluorescently Activated Cell Sorting (FACs) Analysis

This procedure applies to Examples 25-27. For cell sorting assays, iron limited conditions were maintained by addition of dipyridyl to the culture (final concentration of 0.2 nM). Cells were grown to mid-log phase (NB or LB broth), the siderophore conjugates added to 10-20 million CFU of bacterial cells to a final siderophore conjugate concentration of 2-3 uM (total volume=11 mL), and incubated for a period of 30 minutes. Competition was performed by adding a 100-fold excess of desferrioxamine (Yersinia) or pyoverdine PaA (Pseudomonas) to the cells 15 minutes prior to incubation with the siderophore conjugates. Fluorescently activated cell sorting (FACS) was performed on a FACS Caliber (BD Bio systems, Franklin Lakes, N.J.) cell sorter with both the forward scatter and side scatter in the log mode per manufactures guidelines for analyzing bacteria. Bacteria samples were diluted with PBS to achieve 200-400 counts per second.

EXAMPLE 25

FACS Analysis Using Desferrioxamine Fluorescein

Figure 9:
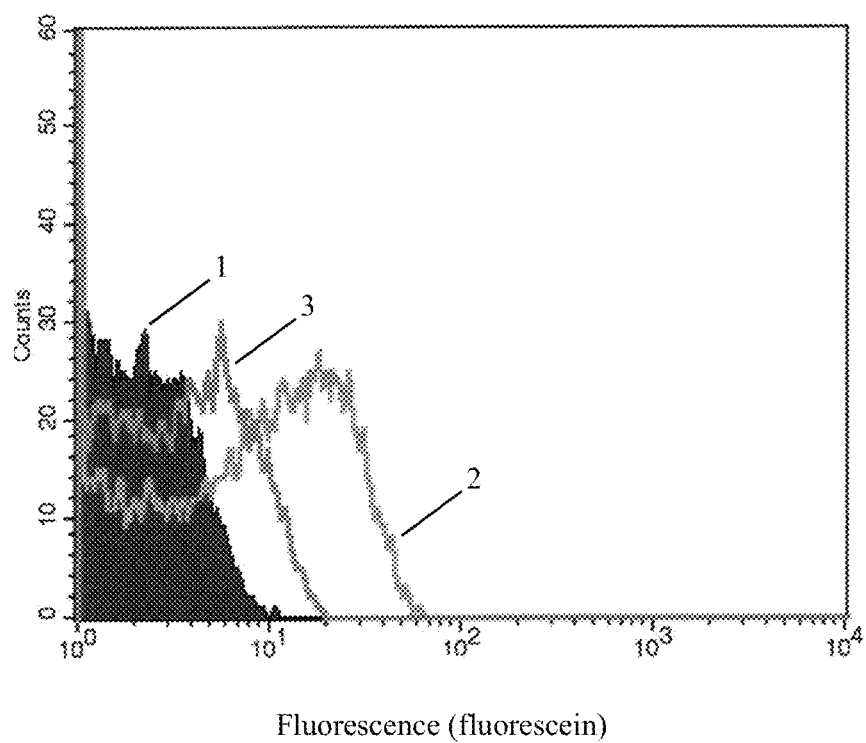
FIG. 9 shows binding and competition of desferrioxamine fluorescein to *Yersinia enterocolitica*.

*Yersinia enterocolitica* incubated in the presence of desferrioxamine fluorescein demonstrated a significant shift in fluorescence intensity (~50% versus 1%; see FIG. 9) as compared to the non-incubated control, which was reduced to 15% by competition with a 100-fold excess of desferrioxamine. In this case, fluorescence shift indicates binding of the fluorescein conjugate to the siderophore receptor on the bacterial surface; whereas, adding excess non-labeled ligand (competition) reduces the number of free binding sites prior to conjugate incubation. Taken together, both results indicate receptor specific binding. It is interesting to note that this compound was iron unloaded and thus consistent with unloaded siderophore binding reported by Schalk et al., Mol. Microbiol. 39: 351-360 (2001).

EXAMPLE 26

FACS Analysis Using Pyoverdine Peptide Fluorescein

Figure 10:
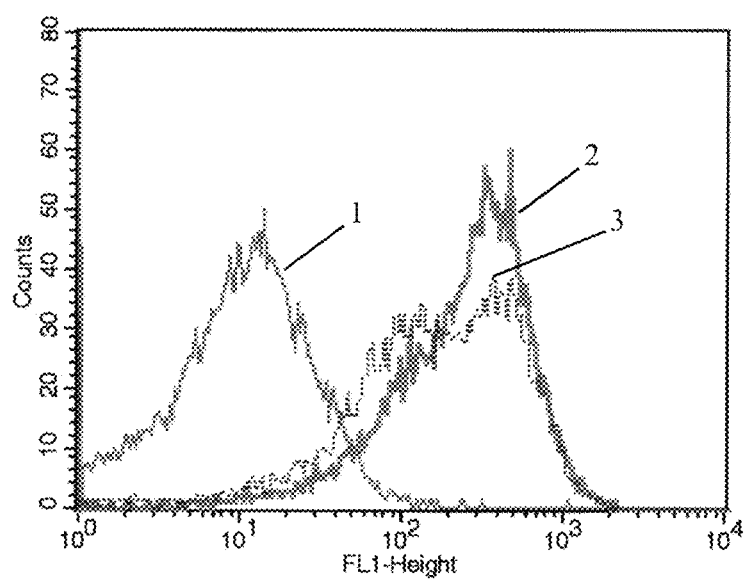
FIG. 10 shows binding and competition of pyoverdine fluorescein peptide to *Pseudomonas aeruginosa*.

Cell studies using FACS analysis and *Pseudomonas aeruginosa* were performed essentially as described under Example 25 (see FIG. 10) to assess binding and competition of this molecule (concentrations ranged from 1 µM to 1 nM). At 0.1 µM, competition using free pyoverdine was detected.

EXAMPLE 27

Detection of *Bacillus* Spores

Figure 7:
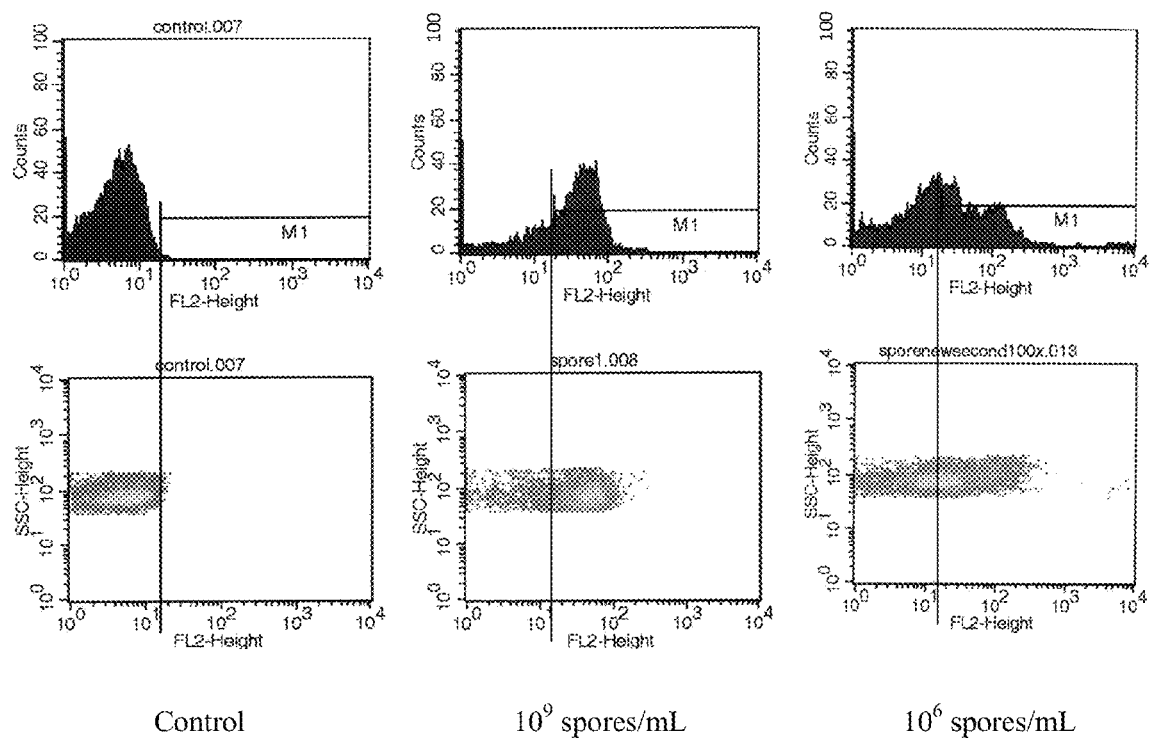
FIG. 7 shows the detection level of *bacillus* spores using a siderophore-peptide conjugate and FACS analysis as described herein.
Figure 8:
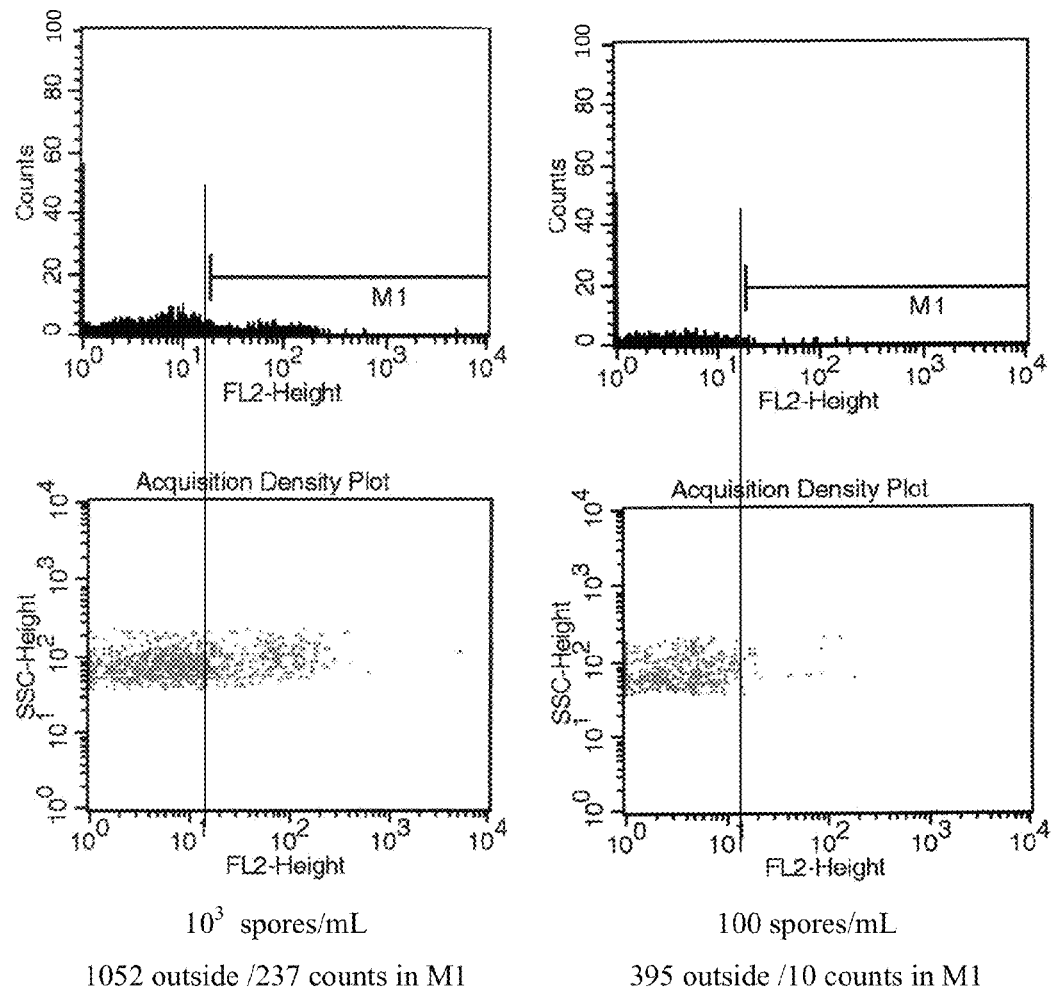
FIG. 8 shows the detection level of *bacillus* spores using a siderophore-peptide conjugate and FACS analysis as described herein.

A stock solution of *bacillus* spores was made and then diluted by factors of 10. When 100 spores were added to 1 ml of solution, 10 spores were detected by flow cytometry indicating a detection level of 10 spores/ml. Thus, spore concentrations of about 40% of the spores added were detectable (see FIGS. 7 and 8). A siderophore-peptide conjugate and FACS analysis as described herein were used.

What is claimed is:

1. A method of diagnosing a disease state mediated by pathogenic cells comprising the step of
   administering to a patient a composition comprising a conjugate or complex of the general formula $A_b$-X wherein the group $A_b$ comprises a ligand that binds to the pathogenic cells and the group X comprises an imaging agent, and wherein the pathogenic cells express a receptor for the ligand and are detected using multiphoton in vivo flow cytometry
   wherein the disease state mediated by the pathogenic cells is diagnosed by detecting the conjugate bound to at least one of the pathogenic cells.

2. The method of claim 1 wherein $A_b$ comprises a folate receptor binding ligand, or an analog or derivative thereof.

3. The method of claim 1 wherein $A_b$ comprises a siderophore or an oligosaccharide.

4. The method of claim 1 wherein the imaging agent comprises a chromophore.

5. The method of claim 4 wherein the chromophore comprises a compound selected from the group consisting of fluorescein, Oregon Green, rhodamine, phycoerythrin, Texas Red, and AlexaFluor 488.

6. The method of claim 1 wherein the patient is suffering from a disease state selected from the group consisting of cancer and a disease state mediated by a microorganism.

7. The method of claim 1 wherein $A_b$-X is selected from the group consisting of folate-fluorescein, folate-Oregon Green, folate-rhodamine, folate-phycoerythrin, folate-cys-Texas Red, and folate-AlexaFluor.

8. The method of claim 3 wherein $A_b$-X is selected from the group consisting of desferrioxamine fluorescein and pyoverdine peptide fluorescein.

9. The method of claim 1 wherein the disease state is cancer.

10. The method of claim 1 wherein the disease state is mediated by a pathogenic microorganism.

11. The method of claim 1 wherein the composition is administered in a parenteral dosage form.

12. The method of claim 1 wherein the composition is administered in an oral dosage form.

13. The method of claim 11 wherein the parenteral dosage form is selected from the group consisting of intraperitoneal, subcutaneous, intramuscular, intravenous, intradermal, and intrathecal dosage forms.

14. The method of claim 1 wherein the composition further comprises a pharmaceutically acceptable carrier.

15. The method of claim 14 wherein the pharmaceutically acceptable carrier is a liquid carrier.

16. The method of claim 15 wherein the liquid carrier is selected from the group consisting of alcohols, glycols, esters, amides, and a combination thereof.

17. The method of claim 15 wherein the liquid comprises an isotonic saline solution or a glucose solution.

18. The method of claim 17 wherein the glucose solution is a 5% glucose solution.

19. The method of claim 11 wherein the conjugate within the composition is lyophilized.

20. The method of claim 7 wherein $A_b$-X is folate-fluorescein.

21. The method of claim 5 wherein the chromophore is fluorescein.

22. The method of claim 5 wherein the chromophore is rhodamine.

23. The method of claim 2 wherein the folate receptor binding ligand, or analog or derivative thereof, is selected from the group consisting of folic acid, folinic acid, pteropolyglutamic acid, a tetrahydropterin, a dihydrofolate, a tetrahydrofolate, a 1-deaza folate, a 3-deaza folate, a 5-deaza folate, an 8-deaza folate, a 10-deaza folate, a 1,5 dideaza folate, a 5,10-dideaza folate, an 8,10-dideaza folate, a 5,8-dideaza folate, aminopterin, amethopterin, N10-methylfolate, 2-deamino-hydroxyfolate, 1-deazamethopterin, 3-deazamethopterin, and 3'5'-dichloro-4-amino-4-deoxy-N10-methylpteroylglutamic acid.

24. A method of detecting cancer cells comprising the step of
administering to a patient a composition comprising a conjugate or complex of the general formula $A_b$-X wherein the group $A_b$ comprises a ligand that binds to the cells and the group X comprises an imaging agent, and wherein the cells express a receptor for the ligand,
wherein the cells are detected using multiphoton in vivo flow cytometry.

25. The method of claim 24 wherein $A_b$ comprises a folate receptor binding ligand, or an analog or derivative thereof.

26. The method of claim 24 wherein the imaging agent comprises a chromophore.

27. The method of claim 26 wherein the chromophore comprises a compound selected from the group consisting of fluorescein, Oregon Green, rhodamine, phycoerythrin, Texas Red, and AlexaFluor 488.

28. The method of claim 24 wherein $A_b$-X is selected from the group consisting of folate-fluorescein, folate-Oregon Green, folate-rhodamine, folate-phycoerythrin, folate-cys-Texas Red, and folate-AlexaFluor.

29. The method of claim 24 wherein the composition is administered in a parenteral dosage form.

30. The method of claim 24 wherein the composition is administered in an oral dosage form.

31. The method of claim 29 wherein the parenteral dosage form is selected from the group consisting of intraperitoneal, subcutaneous, intramuscular, intravenous, intradermal, and intrathecal dosage forms.

32. The method of claim 24 wherein the composition further comprises a pharmaceutically acceptable carrier.

33. The method of claim 32 wherein the pharmaceutically acceptable carrier is a liquid carrier.

34. The method of claim 33 wherein the liquid carrier is selected from the group consisting of alcohols, glycols, esters, amides, and a combination thereof.

35. The method of claim 33 wherein the liquid comprises an isotonic saline solution or a glucose solution.

36. The method of claim 35 wherein the glucose solution is a 5% glucose solution.

37. The method of claim 29 wherein the conjugate within the composition is lyophilized.

38. The method of claim 27 wherein the chromophore is rhodamine.

39. The method of claim 25 wherein the folate receptor binding ligand, or analog or derivative thereof, is selected from the group consisting of folic acid, folinic acid, pteropolyglutamic acid, a tetrahydropterin, a dihydrofolate, a tetrahydrofolate, a 1-deaza folate, a 3-deaza folate, a 5-deaza folate, an 8-deaza folate, a 10-deaza folate, a 1,5 dideaza folate, a 5,10-dideaza folate, an 8,10-dideaza folate, a 5,8-dideaza folate, aminopterin, amethopterin, N10-methylfolate, 2-deamino-hydroxyfolate, 1-deazamethopterin, 3-deazamethopterin, and 3'5'-dichloro-4-amino-4-deoxy-N10-methylpteroylglutamic acid.

* * * * *